US012702659B2

(12) United States Patent
Angel et al.

(10) Patent No.: US 12,702,659 B2

(45) Date of Patent: Aug. 11, 2026

(54) RIFAXIMIN LIQUID FORMULATIONS

(71) Applicant: Bausch Health Ireland Limited, Dublin (IE)

(72) Inventors: Arturo J. Angel, Santa Rosa, CA (US); Kasturi R. Pawar, Rohnert Park, CA (US); Radhakrishnan S. Pillai, Santa Rosa, CA (US)

(73) Assignee: Bausch Health Ireland Limited, Dublin (IE)

( * ) Notice: Subject to any disclaimer, the term of this patent is extended or adjusted under 35 U.S.C. 154(b) by 1000 days.

(21) Appl. No.: 17/763,615

(22) PCT Filed: Sep. 24, 2020

(86) PCT No.: PCT/EP2020/076746

§ 371 (c)(1),
(2) Date: Mar. 24, 2022

(87) PCT Pub. No.: WO2021/058656

PCT Pub. Date: Apr. 1, 2021

(65) Prior Publication Data

US 2022/0378758 A1 Dec. 1, 2022

Related U.S. Application Data

(60) Provisional application No. 63/044,447, filed on Jun. 26, 2020, provisional application No. 62/904,790, filed on Sep. 24, 2019.

(51) Int. Cl.

| | |
|---|---|
| ***A61K 31/437*** | (2006.01) |
| ***A61K 9/48*** | (2006.01) |
| ***A61P 31/04*** | (2006.01) |

(52) U.S. Cl.

CPC .......... *A61K 31/437* (2013.01); *A61K 9/4825* (2013.01); *A61K 9/4858* (2013.01); *A61K 9/4866* (2013.01); *A61P 31/04* (2018.01)

(58) Field of Classification Search

CPC .............................. A61K 31/437; A61P 31/04
See application file for complete search history.

(56) References Cited

U.S. PATENT DOCUMENTS

| | | | |
|---|---|---|---|
| 4,717,569 A | 1/1988 | Harrison et al. | |
| 5,352,679 A | 10/1994 | Ferrieri et al. | |
| 6,861,053 B1 | 3/2005 | Lin et al. | |
| 7,915,275 B2 | 3/2011 | Viscomi et al. | |
| 8,003,118 B2 | 8/2011 | Kodsi | |
| 8,309,569 B2 | 11/2012 | Forbes et al. | |
| 8,383,151 B2 | 2/2013 | Jahagirdar et al. | |
| 8,946,252 B2 | 2/2015 | Forbes et al. | |
| 9,133,217 B2 | 9/2015 | Parent et al. | |
| 10,137,114 B2 | 11/2018 | Jahagirdar et al. | |
| 11,779,571 B2 | 10/2023 | Forbes et al. | |
| 2004/0034021 A1* | 2/2004 | Michaelis ............. | A61K 47/12 514/229.5 |
| 2009/0028940 A1 | 1/2009 | Jahagirdar et al. | |
| 2012/0196887 A1 | 8/2012 | Darkoh et al. | |
| 2012/0214833 A1 | 8/2012 | Kulkarni et al. | |
| 2013/0184302 A1 | 7/2013 | Bortey et al. | |
| 2013/0210852 A1 | 8/2013 | DuPont et al. | |
| 2014/0221414 A1 | 8/2014 | Kulkarni et al. | |
| 2015/0164866 A1 | 6/2015 | Randall | |
| 2016/0024051 A1 | 1/2016 | Genov et al. | |
| 2016/0243144 A1 | 8/2016 | Garegnani et al. | |
| 2017/0087134 A1 | 3/2017 | Golden | |
| 2017/0333562 A1 | 11/2017 | Selbo et al. | |
| 2018/0021297 A1 | 1/2018 | Hauser | |
| 2018/0049979 A1 | 2/2018 | Zhao et al. | |
| 2018/0243272 A1 | 8/2018 | Forbes et al. | |
| 2019/0224175 A1 | 7/2019 | Golden | |
| 2023/0027192 A1 | 1/2023 | Bajaj | |
| 2023/0277447 A1 | 9/2023 | Cole et al. | |

FOREIGN PATENT DOCUMENTS

| | | |
|---|---|---|
| CN | 101137350 B | 3/2008 |
| CN | 101502513 A | 8/2009 |
| CN | 102716168 A | 10/2012 |
| CN | 103118666 A | 5/2013 |
| CN | 103263523 A | 8/2013 |
| CN | 103263668 A | 8/2013 |
| CN | 105025717 A | 11/2015 |
| CN | 110290781 A | 9/2019 |
| EP | 2011486 A1 | 1/2009 |
| EP | 1996710 B1 | 8/2019 |
| JP | 2002537317 A | 11/2022 |
| RU | 2609833 C2 | 10/2015 |
| WO | 2003/101445 A1 | 12/2003 |

(Continued)

OTHER PUBLICATIONS

Hecht et al., In Vitro Activities of 15 Antimicrobial Agents against 110 Toxigenic Clostridium difficile Clinical Isolates Collected from 1983 to 2004, Antimicrob Agents Chemother. May 21, 2007;51(8):2716-2719.*

Office Action issued in corresponding Mexican Application No. MX/a/2022/003481 dated Oct. 18, 2024, 12 pages.

Office Action issued in Russian Patent Application No. 2022110800, dated Jan. 23, 2024, 26 pages.

Arya et al. Rifaximin—the promising anti-microbial for enteric infections. J Infect. 51(3): 262, Abstract only (2005).

Cober et al. Stability of extemporaneously prepared rifaximin oral suspensions. Am J Health Syst Pharm. 67(4):287-9 (2010).

(Continued)

*Primary Examiner* — Svetlana M Ivanova

(74) *Attorney, Agent, or Firm* — Morgan, Lewis & Bockius LLP

(57) ABSTRACT

Provided herein are pharmaceutical compositions which enhance the intestinal levels of soluble rifaximin, formulations comprising said compositions, and their use in treating one or more bowel related disorders.

21 Claims, 11 Drawing Sheets

(56) References Cited

FOREIGN PATENT DOCUMENTS

| | | | | |
|---|---|---|---|---|
| WO | WO-03101445 | A1 * | 12/2003 | ............ A61K 31/33 |
| WO | 200473692 | A1 | 9/2004 | |
| WO | 2005/030142 | A2 | 4/2005 | |
| WO | 2005044823 | A2 | 5/2005 | |
| WO | 2006/094737 | A2 | 9/2006 | |
| WO | 2006094662 | A1 | 9/2006 | |
| WO | WO-2007117556 | A2 * | 10/2007 | .......... A61K 31/355 |
| WO | 2008016708 | A2 | 2/2008 | |
| WO | 2009/008005 | A1 | 1/2009 | |
| WO | 2010044093 | A1 | 4/2010 | |
| WO | 2010067072 | A1 | 6/2010 | |
| WO | 2011/051971 | A2 | 5/2011 | |
| WO | 2012035283 | A1 | 3/2012 | |
| WO | 2012/103119 | A1 | 8/2012 | |
| WO | 2006112541 | A1 | 7/2013 | |
| WO | 2014006576 | A1 | 1/2014 | |
| WO | 2016/014437 | A1 | 1/2016 | |
| WO | 2016140952 | A1 | 9/2016 | |
| WO | 2017205302 | A1 | 11/2017 | |
| WO | 2018064472 | A1 | 4/2018 | |
| WO | 2018165404 | A1 | 9/2018 | |

OTHER PUBLICATIONS

Office Action issued in European Patent Application No. 21739302.4, dated Jun. 13, 2024, 11 pages.
Office Action issued in Chinese Patent Application No. 202180052294.0, dated Mar. 27, 2024, 30 pages.
Kornbluth Asher et al.: "Efficacy and Safety of Rifaximin in the Treatment of Mild-Moderate Crohn's Disease: Results of An Ope••Label Pilot Study", Gastroenterology, vol. 128, No. 4 Suppl 2, Apr. 1, 2005, pp. A-579, XP93138544.
Office Action issued in Japanese Patent Application No. 2022-518665, mailed Oct. 1, 2024, 9 pages.
Lu Bin, People's Health Publishing House, New Techniques and New Dosage Forms of Drugs, 2nd version in Jul. 2005, date of publication: May 31, 2005, pp. 51-53.
Office Action issued in European Patent Application No. 19163419.5, dated Mar. 13, 2024, 6 pages.
Prantera et al: "Antibiotic treatment of Crohn's disease: results of a multicentre, double blind, randomized, placebo• controlled trial with rifaximin", Alimentary Pharmacology & Therapeutics, Blackwell Scientific Publications Ltd., Cambridge, GB, vol. 23, No. 8, Mar. 30, 2006, pp. 1117-1125, XP071540572.
Office Action issued in U.S. Appl. No. 18/628,353, dated Aug. 22, 2024, 14 pages.
Office Action issued in U.S. Appl. No. 18/628,366, dated Sep. 17, 2024, 16 pages.
Kornbluth Asher: "Efficacy and Safety of Open Label Rifaximin in the Treatment of Mild-Moderate Crohn's Disease (CD) Refractory to Multiple Medical Therapies", American College of Gastroenterology, vol. 111, Sep. 1, 2006, p. S449, XP93138081.
Sharara et al., A Randomized Double-Blind Placebo-Controlled Trial of Rifaximin in Patients with Abdominal Bloating and Flatulence, Am J Gastroenterol, 101:326-333, 2006.
Scarpignato, Rifaximin, a Poorly Absorbed Antibiotic: Pharmacology and Clinical Potential, Chemotherapy, 51(suppl 1):36-66, 2005.
Marchina et al., Infectious diarrhea in the aged: controlled clinical trial of Rifaximin, Chemioterapia, 7(5):336-40, 1988.
Nikolett Kallai et al: "Evaluation of Drug Release From Coated Pellets Based on Isomalt, Sugar, and Microcrystalline Cellulose Inert Cores", AAPS Pharmscitech, vol. 11, No. 1, Mar. 1, 2010, pp. 383-391, XP055024443, ISSN: 1530-9932, DOI: 10.1208/s12249-010-9396-x.
Bhavik Solanki et al: "Multiple Unit Dosage Forms: a Review", Pharmtechmedica, vol. 1, No. 1, Jan. 1, 2012, pp. 11-21, XP055235562.
Lim Seah H. et al: "Rifaximin for sickle cell disease", American Journal of Hematology vol. 94, No. 12 Oct. 7, 2019, XP055816244, US ISSN: 0361-8609, DOI: 10.1002/ajh.25637 Retrieved from the Internet: URL:https://onlinelibrary.wiley.com/doi/full-XML/10.1002/ajh.25637.
Viscomi G C et al: "Crystal forms of rifaximin and their effect on pharmaceutical properties", Crystengcomm, Royal Society of Chemistry, Cambridge, GB, vol. 10, Jan. 1, 2008, pp. 1074-1081, XP009152378, ISSN: 1466-8033, DOI: 10.1039/B717887E.
Carmelo Scarpignato et al.: "Impact of crystal polymorphism on the systemic bioavailability of rifaximin, an antibiotic acting locally in the gastrointestinal tract, in healthy volunteers", Drug Design, Development and Therapy, Dec. 1, 2014, p. 1, XP055297628, DOI: 10.2147/DDDT.S72572.
Siepmann et al: "Polymer blends for controlled release coatings", Journal of Controlled Release, Elsevier, Amsterdam, NL, vol. 125, No. 1, Oct. 13, 2007, pp. 1-15, XP022375058, ISSN: 0168-3659, DOI: 10.1016/J.JCONREL.2007.09.012.
Office Action issued in Brazilian Patent Application No. BR112022003500-4, dated Sep. 3, 2024, 5 pages.
Decision of Rejection issued in Chinese Patent Application No. 202080067056.2, dated Sep. 9, 2024, 21 pages.
Office Action issued in Chinese Patent Application No. 202180052294.0, dated Nov. 6, 2024, 18 pages.
Office Action issued in U.S. Appl. No. 18/012,362, dated Feb. 12, 2025, 12 pages.
Office Action issued in European Patent Application No. 20785690.7, dated Apr. 17, 2024, 7 pages.
Office Action issued in Chinese Patent Application No. 202080067056.2, dated Apr. 26, 2024, 12 pages.
Decision on Grant issued in Russian Patent Application No. 2022110800, dated Jul. 1, 2024, 25 pages.
Decision on Rejection issued in Chinese Patent Application No. 202080067056.2, dated Sep. 9, 2024, 21 pages.
Office Action issued in Canadian Patent Application No. 3, 151,010, dated Nov. 14, 2023, 5 pages.
International Search Report and Written Opinion issued in PCT/EP2020/076746, dated Jan. 12, 2021, 13 pages.
Omez® DSR Label (LP-003998-061216. Dec. 6, 2016). State Register of Medicines [online] [retrieved Aug. 31, 2023]. Found on <https://grls.rosminzdrav.ru/Instrlmg/2016/12/13/1413974/%D0%9B%D0%9F- 003998[2016]_0.pdf>, 27 pages.
Office Action issued in Eurasian Patent Application No. 202390175, dated May 22, 2025, 10 pages.
Office Action issued in Japanese Patent Application No. 2022-580309, mailed Jul. 15, 2025, 7 pages.
Office Action issued in Canadian Patent Application. No. 3,151,010, dated Sep. 5, 2025, 3 pages.
Office Action issued in Japanese Patent Application No. 2022-518665, dated Apr. 1, 2025, 9 pages.
Cosmetic Ingredient Information Online "PEG-60 Hydrogenated Castor Oil," https://cosmetic-ingredients.org/surfactants-emulsifying-agents/2066/.
Office Action issued in Mexican Patent Application No. MX/a/2022/003481, dated Apr. 22, 2025, 12 pages.
Decision of Rejection issued in Chinese Patent Application No. 202180052294.0, dated Apr. 7, 2025, 31 pages.
Office Action issued in U.S. Appl. No. 17/779,865, dated Mar. 13, 2025, 25 pages.
Vlachogiannakos et al., "Long-term administration of rifaximin improves the prognosis of patients with decompensated alcoholic cirrhosis," Journal of Gastroenterology and Hepatology, 2012, 450-455.
Office Action issued in corresponding Chinese Application No. 202180052294.0, dated Nov. 6, 2024, 18 pages.
Shayto, R.H, Mrad, R.A., and Sharara, A.I., Use of rifaximin in gastrointestinal and liver diseases, World Journal of Gastroenterology, 22, p. 6638-6651 (Year: 2016).
Calanni, F., Renzulli, C., Barbanti, M., and Viscomi, G.C., Rifaximin: beyond the traditional antibiotic acitivty, The Journal of Antibiotics, 67, p. 667-670 (Year: 2014).
Li, T. and Chiang, J.Y.L., Bile Acid Signaling in Metabolic Disease and Drug Therapy, Pharmacological Reviews, 66, p. 948-983 ( Year: 2014).
Hughes, J.P., Rees, S., Kalindjian, S.B., Philpott, K.L., Principles of early drug discovery, British Journal of Pharmacology, 162, p. 1239-1249 (Year: 2011).

(56) References Cited

OTHER PUBLICATIONS

Office Action issued in U.S. Appl. No. 18/241,355, dated Jan. 21, 2026, 15 pages.
Office Action issued in Australian Patent Application No. 2020355603, dated Aug. 22, 2025, 4 pages.
Office Action issued in U.S. Appl. No. 17/779,865, dated Sep. 19, 2025, 12 pages.
Bausch Health Americas, Inc., "Multicenter, Randomized, Double-Blind, Placebo-Controlled Study to Assess The Efficacy and Safety of Three Different Doses (275, 550 AND 1100 MG) of Rifaximin Administered BID For Either Two or Four Weeks in The Treatment of Patients With Diarrhea-Associated Irritable Bowel Syndrome", Version 12 (Dec. 6, 2007). Retrieved from the internet: https://clinicaltrials.gov/study/NCT00269412.
Canadian preliminary appeal decision issued in Canadian Patent Application No. 2,716,578 dated Nov. 28, 2025, 28 pages.
Pimentel et al. "The Effect of a Nonabsorbed Oral Antibiotic (Rifaximin) on the Symptoms of Irritable Bowel Syndrome," Annals of Internal Medicine, 2006, 145, pp. 557-563.
Press release by Salix Pharmaceuticals, Ltd., "Rifaximin Demonstrates Statistically Significant Improvement in Co-Primary Endpoints in Treatment of Diarrhea-Associated Irritable Bowel Syndrome in Phase IIb Study," Sep. 2007.
Examination Report issued in Australian Patent Application No. 2021298178, mailed Jun. 2, 2026, 5 pages.
Office Action issued in U.S. Appl. No. 17/779,865, dated Mar. 10, 2026, 10 pages.
Notice of Acceptance issued in Australian Patent Application No. 2020355603, dated Jan. 28, 2026, 3 pages.

* cited by examiner

RIFAXIMIN LIQUID FORMULATIONS

RELATED APPLICATIONS

This application is a 35 U.S.C. § 371 national stage filing of International Application No. PCT/EP2020/076746, filed on Sep. 24, 2020, which claims priority to U.S. Provisional Application No. 62/904,790, filed Sep. 24, 2019 and U.S. Provisional Application No. 63/044,447, filed on Jun. 26, 2020. The entire contents of each of the foregoing applications are incorporated herein by reference.

BACKGROUND

Rifaximin (e.g., Xifaxan®) is an orally available broad spectrum antibiotic with antimicrobial activity against Gram-positive and Gram-negative aerobic and anaerobic bacteria. Rifaximin is currently indicated for the treatment of traveler's diarrhea (TD), for maintaining remission of hepatic encephalopathy (HE), and for treating irritable bowel syndrome with diarrhea (IBS-D). Other uses for rifaximin include e.g., treating *C. difficile* infections, infectious diarrhea, small intestinal bacterial overgrowth (SIBO), inflammatory disease, inflammatory bowel disease (IBD), and diverticular disease. Because rifaximin is largely water-insoluble and poorly absorbed, systemic effects are unusual. For example, less than 0.5% of rifaximin is absorbed into the bloodstream when taken orally. This translates to a highly favorable safety profile that is comparable to placebo. Rifaximin is, however, increasingly soluble in bile. This results in higher luminal concentrations and enhanced antimicrobial effects against enteric bacteria. Larger effects in the small intestine as well as low microbial resistance and minimal effect on colonic microflora are also seen. As such, rifaximin is highly favored for use against conditions associated with the small intestine as well as for long term use (e.g., 6 months for longer or in instances where bacterial resistance is of concern).

Yet, even with these beneficial features, over 90% of rifaximin is excreted in feces almost entirely as unchanged drug. In addition, because systemic availability is low, rifaximin has traditionally been overlooked for treating systemic infections caused by invasive organisms. Patient compliance is a further concern since low adsorption leads to larger, more frequent dosing. Currently, rifaximin is manufactured as 200 mg and 550 mg tablets and is approved for administration at daily dosages of 600 mg (for TD) or 1650 mg (for HE).

There is a need for rifaximin formulations that improve the availability of soluble rifaximin to the stomach, small intestine, and/or large intestine.

SUMMARY

In an embodiment, the invention described herein includes a composition comprising rifaximin, a hydrogenated castor oil, and at least one additional solubilizing excipient. In some embodiments, the compositions described herein include a low dose rifaximin. In some embodiments, the compositions described herein may be pharmaceutically acceptable compositions. In an embodiment, the invention described herein includes a pharmaceutically acceptable composition comprising low dose rifaximin, a hydrogenated castor oil, and at least one additional solubilizing excipient.

In some embodiments, the hydrogenated castor oil may be polyoxyl 40 hydrogenated castor oil (e.g., Cremophor® RH-40).

In some embodiments, the hydrogenated castor oil may be present in an amount ranging from about 25% to about 65% by weight of the composition.

In some embodiments, the hydrogenated castor oil may be present in an amount ranging from about 25% to about 50% by weight of the composition.

In some embodiments, the hydrogenated castor oil may be present in an amount ranging from about 30% to about 45% by weight of the composition.

In some embodiments, the hydrogenated castor oil may be present in an amount ranging from about 35% to about 40% by weight of the composition. In some embodiments, the hydrogenated castor oil may be present in an amount of about 35% or about 40% by weight of the composition.

In some embodiments, the hydrogenated castor oil may be present in an amount ranging from about 45% to about 65% by weight of the composition.

In some embodiments, the at least one additional solubilizing excipient may be a plurality of additional solubilizing excipients. In some embodiments, the at least one additional solubilizing excipient may be selected from the group consisting of a water-soluble organic solvent, a non-ionic surfactant, a water-insoluble lipid, long-chain triglycerides, and combinations thereof. In some embodiments, the at least one additional solubilizing excipient may comprise one or more of a water-soluble organic solvent, a non-ionic surfactant, a water-insoluble lipid, and long-chain triglycerides. In some embodiments, the at least one additional solubilizing excipient may be selected from the group consisting of polyethylene glycol 600, glyceryl caprylate, polysorbate 80, castor oil, benzyl alcohol, polyethylene glycol 400, diethylene glycol monoethyl ether, glyceryl monooleate, triethylene glycol, diisopropyl adipate, diethyl sebacate, oleyl alcohol, and combinations thereof. In some embodiments, the at least one additional solubilizing excipient may comprise one or more of polyethylene glycol 600, glyceryl caprylate, polysorbate 80, castor oil, benzyl alcohol, polyethylene glycol 400, diethylene glycol monoethyl ether, glyceryl monooleate, triethylene glycol, diisopropyl adipate, diethyl sebacate, and oleyl alcohol.

In some embodiments, the at least one additional solubilizing excipient may be one or more additional solubilizing excipients that allows for or otherwise provides for a rifaximin saturation solubility of greater than about 10% by weight of the rifaximin in the composition. In some embodiments, the at least one additional solubilizing excipient may be one or more additional solubilizing excipients that allows for or otherwise provides for a rifaximin saturation solubility of greater than about 14% by weight of the rifaximin in the composition.

In some embodiments, the at least one additional solubilizing excipient may be selected from the group consisting of polyethylene glycol 600, glyceryl caprylate, polysorbate 80, castor oil, benzyl alcohol, polyethylene glycol 400, diethylene glycol monoethyl ether, glyceryl monooleate, triethylene glycol, diisopropyl adipate, diethyl sebacate, oleyl alcohol, polysorbate 20, oleic acid, caprylic capric triglycerides, propylene glycol, sesame oil, soybean oil, corn oil, and combinations thereof. In some embodiments, the at least one additional solubilizing excipient may comprise at least one of polyethylene glycol 600, glyceryl caprylate, polysorbate 80, castor oil, benzyl alcohol, polyethylene glycol 400, diethylene glycol monoethyl ether, glyceryl monooleate, triethylene glycol, diisopropyl adipate, diethyl sebacate, oleyl alcohol, polysorbate 20, oleic acid, caprylic capric triglycerides, propylene glycol, sesame oil, soybean oil, and corn oil.

In some embodiments, the at least one additional solubilizing excipient may be selected from the group consisting of castor oil, glyceryl caprylate, polysorbate 80, diethyl sebacate, diethylene glycol monoethyl ether, and combinations thereof. In some embodiments, the at least one additional solubilizing excipient may comprise one or more of castor oil, glyceryl caprylate, polysorbate 80, and diethyl sebacate.

In some embodiments, the at least one additional solubilizing excipient may be present in an amount ranging from about 25% to about 65% by weight of the composition.

In some embodiments, the at least one additional solubilizing excipient may be present in an amount ranging from about 30% to about 65% by weight of the composition.

In some embodiments, the at least one additional solubilizing excipient may be present in an amount ranging from about 35% to about 65% by weight of the composition.

In some embodiments, the at least on additional solubilizing excipient may be present in an amount ranging from about 40% to about 65% by weight of the composition.

In some embodiments, the at least one additional solubilizing excipient may be present in an amount ranging from about 45% to about 65% by weight of the composition.

In some embodiments, the at least one additional solubilizing excipient may be present in an amount ranging from about 50% to about 65% by weight of the composition.

In some embodiments, the at least one additional solubilizing excipient may be present in an amount ranging from about 50% to about 60% by weight of the composition.

In some embodiments, the at least one additional solubilizing excipient may be present in an amount ranging from about 55% to about 60% by weight of the composition.

In some embodiments, the at least one additional solubilizing excipient may be present in an amount ranging from about 55% to about 65% by weight of the composition.

In some embodiments, the at least one additional solubilizing excipient may be present in an amount ranging from about 60% to about 65% by weight of the composition.

In some embodiments, the at least one additional solubilizing excipient may be present in an amount ranging from about 62% to about 63% by weight of the composition.

In some embodiments, the at least one additional solubilizing excipient may be a combination of at least two additional solubilizing excipients. In some embodiments, the at least one additional solubilizing excipient may be a combination of at least three additional solubilizing excipients. In some embodiments, the at least one additional solubilizing excipient comprises castor oil and glyceryl caprylate. In some embodiments, the at least one additional solubilizing excipient comprises castor oil and polysorbate 80. In some embodiments, the at least one additional solubilizing excipient comprises glyceryl caprylate and polysorbate 80. In some embodiments, the at least one additional solubilizing excipient comprises castor oil, glyceryl caprylate, and polysorbate 80. In some embodiments, the at least one additional solubilizing excipient is a combination of castor oil, glyceryl caprylate, and polysorbate 80.

In some embodiments, the compositions described herein include castor oil in an amount ranging from about 5% to about 15% by weight of the composition; glyceryl caprylate in an amount ranging from about 5% to about 15% by weight of the composition; and polysorbate 80 in an amount ranging from about 20% to about 40% by weight of the composition.

In some embodiments, the compositions described herein include castor oil in an amount ranging from about 5% to about 15% by weight of the composition; glyceryl caprylate in an amount ranging from about 5% to about 15% by weight of the composition; and polysorbate 80 in an amount ranging from about 20% to about 40% by weight of the composition.

In some embodiments, the compositions described herein include castor oil in an amount ranging from about 8% to about 12% by weight of the composition; glyceryl caprylate in an amount ranging from about 10% to about 14% by weight of the composition; and polysorbate 80 in an amount ranging from about 30% to about 35% by weight of the composition.

In some embodiments, the compositions described herein include castor oil in an amount ranging from about 10% to about 20% by weight of the composition; glyceryl caprylate in an amount ranging from about 5% to about 15% by weight of the composition; and polysorbate 80 in an amount ranging from about 20% to about 40% by weight of the composition.

In some embodiments, the compositions described herein include castor oil in an amount ranging from about 13% to about 18% by weight of the composition; glyceryl caprylate in an amount ranging from about 10% to about 14% by weight of the composition; and polysorbate 80 in an amount ranging from about 30% to about 35% by weight of the composition.

In some embodiments, the compositions described herein include castor oil in an amount ranging from about 5% to about 15% by weight of the composition; glyceryl caprylate in an amount ranging from about 10% to about 15% by weight of the composition; and polysorbate 80 in an amount ranging from about 35% to about 45% by weight of the composition.

In some embodiments, the compositions described herein include castor oil in an amount ranging from about 8% to about 12% by weight of the composition; glyceryl caprylate in an amount ranging from about 10% to about 15% by weight of the composition; and polysorbate 80 in an amount ranging from about 38% to about 42% by weight of the composition.

In some embodiments, the at least one additional solubilizing excipient comprises diethyl sebacate and diethylene glycol monoethyl ether. In some embodiments, the at least one additional solubilizing excipient comprises diethyl sebacate and diethylene glycol monoethyl ether. In some embodiments, the at least one additional solubilizing excipient is a combination of diethyl sebacate and diethylene glycol monoethyl ether. In some embodiments, the at least one additional solubilizing excipient is a combination of diethyl sebacate and diethylene glycol monoethyl ether.

In some embodiments, the compositions described herein include diethyl sebacate in an amount ranging from about 20% to about 35% by weight of the composition; and diethylene glycol monoethyl ether in an amount ranging from about 20% to about 35% by weight of the composition. In some embodiments, the compositions described herein include diethyl sebacate in an amount ranging from about 20% to about 35% by weight of the composition; and diethylene glycol monoethyl ether in an amount ranging from about 20% to about 35% by weight of the composition.

In some embodiments, the compositions described herein include diethyl sebacate in an amount ranging from about 25% to about 30% by weight of the composition; and diethylene glycol monoethyl ether in an amount ranging from about 25% to about 30% by weight of the composition.

In some embodiments, the compositions described herein include diethyl sebacate in an amount ranging from about 25% to about 30% by weight of the composition; and diethylene glycol monoethyl ether in an amount ranging from about 25% to about 30% by weight of the composition.

In some embodiments, the compositions described herein include diethyl sebacate in an amount ranging from about 10% to about 20% by weight of the composition; and diethylene glycol monoethyl ether in an amount ranging from about 30% to about 45% by weight of the composition. In some embodiments, the compositions described herein include diethyl sebacate in an amount ranging from about 10% to about 20% by weight of the composition; and diethylene glycol monoethyl ether in an amount ranging from about 30% to about 45% by weight of the composition.

In some embodiments, the compositions described herein include diethyl sebacate in an amount ranging from about 14% to about 18% by weight of the composition; and diethylene glycol monoethyl ether in an amount ranging from about 36% to about 40% by weight of the composition. In some embodiments, the compositions described herein include diethyl sebacate in an amount ranging from about 14% to about 18% by weight of the composition; and diethylene glycol monoethyl ether in an amount ranging from about 36% to about 40% by weight of the composition.

In some embodiments, the compositions described herein may include an antioxidant and/or chelating agent. In some embodiments, the compositions described herein may include an antioxidant and/or chelating agent selected from the group consisting of ascorbyl palmitate, butylated hydroxyanisole, butylated hydroxytoluene (BHT), citric acid, potassium metabisulfite, sodium metabisulfite, cysteine, propyl gallate, sodium thiosulfate, vitamin E, 3,4-dihydroxybenzoic acid, and a combination thereof. In some embodiments, the compositions described herein may include one or more of ascorbyl palmitate, butylated hydroxyanisole, butylated hydroxytoluene (BHT), citric acid, potassium metabisulfite, sodium metabisulfite, propyl gallate, sodium thiosulfate, cysteine, vitamin E, and 3,4-dihydroxybenzoic acid.

In some embodiments, the compositions described herein may include an antioxidant in an amount ranging from about 0.01% to about 0.1% by weight of the composition.

In some embodiments, the compositions described herein may include BHT.

In some embodiments, the compositions described herein may include BHT in an amount ranging from about 0.01% to about 0.1% by weight of the composition.

In some embodiments, the compositions described herein may include citric acid.

In some embodiments, the compositions described herein may include citric acid in an amount ranging from about 0.01% to about 0.1% by weight of the composition.

In some embodiments, the compositions described herein may include ascorbyl palmitate.

In some embodiments, the compositions described herein may include ascorbyl palmitate in an amount ranging from about 0.05% to about 0.15% by weight of the composition.

In some embodiments, the compositions described herein may include BHT and citric acid.

In some embodiments, the compositions described herein may include BHT and citric acid each in an amount ranging from about 0.01% to about 0.1% by weight of the composition.

In some embodiments, the compositions described herein may include BHT, citric acid, and ascorbyl palmitate.

In some embodiments, the compositions described herein may include BHT, citric acid, and ascorbyl palmitate, each in an amount ranging from about 0.05% to about 0.15% by weight of the composition.

In some embodiments, the compositions described herein may include rifaximin in an amount ranging from about 2.5% to about 15% by weight of the composition.

In some embodiments, the compositions described herein may include rifaximin in an amount ranging from about 2.5% to about 12% by weight of the composition.

In some embodiments, the compositions described herein may include rifaximin in an amount ranging from about 5% to about 10% by weight of the composition.

In some embodiments, the compositions described herein may include rifaximin in an amount ranging from about 1.0% to about 15% by weight of the composition.

In some embodiments, the compositions described herein may include rifaximin in an amount ranging from about 1.0% to about 5% by weight of the composition.

In some embodiments, the compositions described herein may include rifaximin in an amount that is less than about 125 mg. In some embodiments, the compositions described herein may include rifaximin in an amount ranging from about 10 mg to about 125 mg. In some embodiments, the compositions described herein may include rifaximin in an amount ranging from about 25 mg to about 125 mg. In some embodiments, the compositions described herein may include rifaximin in an amount ranging from about 25 mg to about 75 mg. In some embodiments, the compositions described herein may include rifaximin in an amount ranging from about 75 mg to about 125 mg. In some embodiments, the compositions described herein may include rifaximin in an amount of about 50 mg. In some embodiments, the compositions described herein may include rifaximin in an amount of about 100 mg.

In some embodiments, the compositions described herein may include rifaximin in an amount that is less than about 125 mg. In some embodiments, the compositions described herein may include rifaximin in an amount ranging from about 1 mg to about 50 mg. In some embodiments, the compositions described herein may include rifaximin in an amount ranging from about 1 mg to about 25 mg. In some embodiments, the compositions described herein may include rifaximin in an amount ranging from about 1 mg to about 10 mg. In some embodiments, the compositions described herein may include rifaximin in an amount ranging from about 1 mg to about 5 mg. In some embodiments, the compositions described herein may include rifaximin in an amount of about 2 mg to about 5 mg. In some embodiments, the compositions described herein may include rifaximin in an amount of about 3 mg to about 4 mg.

In an embodiment, the invention may include a composition comprising about 10% rifaximin, about 10% castor oil, about 12% glyceryl caprylate, about 33% polysorbate 80, and about 35% polyoxyl 40 hydrogenated castor oil, by weight of the composition. In an embodiment, the invention may include a composition comprising about 10% rifaximin, about 10% castor oil, about 12% glyceryl caprylate, about 33% polysorbate 80, and about 35% polyoxyl 40 hydrogenated castor oil, by weight of the composition.

In an embodiment, the invention may include a composition comprising about 10% rifaximin, about 35% polyoxyl 40 hydrogenated castor oil, about 27.5% diethyl sebacate, and about 27.5% diethylene glycol monoethyl ether, by weight of the composition.

In an embodiment, the invention may include a composition comprising about 5% rifaximin, about 15% castor oil, about 12% glyceryl caprylate, about 33% polysorbate 80, and about 35% polyoxyl 40 hydrogenated castor oil, by weight of the composition.

In an embodiment, the invention may include a composition comprising about 10% rifaximin, about 40% polyoxyl 40 hydrogenated castor oil, about 16.5% diethyl sebacate, and about 38.5% diethylene glycol monoethyl ether, by weight of the composition.

In an embodiment, the invention may include a composition comprising about 2.5% rifaximin, about 10% castor oil, about 12% glyceryl caprylate, about 40% polysorbate 80, and about 35% polyoxyl 40 hydrogenated castor oil, by weight of the composition.

In some embodiments, the compositions described herein are liquid compositions. In some embodiments, the compositions described herein may be formulated in a soft capsule dosage form. In some embodiments, the compositions described herein may be liquid compositions formulated in a soft capsule dosage form. In some embodiments, the compositions described herein may be formulated in a hard capsule dosage form. In some embodiments, the compositions described herein may be liquid compositions formulated in a hard capsule dosage form. In some embodiments, the compositions described herein may be formulated in a gelatin capsule dosage form. In some embodiments, the compositions described herein may be liquid compositions formulated in a gelatin capsule dosage form.

In an embodiment, the invention includes methods of treating one or more diseases in a subject in need thereof, comprising the step of administering to the subject a therapeutically effective amount of a composition as described herein. In some embodiments, the one or more diseases may include bowel-related or liver function disorders. In some embodiments, the invention includes methods of treating one or more bowel-related or liver function disorders in a subject in need thereof, comprising the step of administering to the subject a therapeutically effective amount of a composition as described herein. In some embodiments, the one or more bowel-related or liver function disorders may be selected from the group consisting of irritable bowel syndrome (IBS), such as IBS-D, diarrhea, microbe associated diarrhea, infectious diarrhea, *Clostridium difficile* infections and symptoms, travelers' diarrhea, small intestinal bacterial overgrowth (SIBO), Crohn's disease, diverticular disease, pancreatitis, pancreatic insufficiency, enteritis, ulcerative colitis, antibiotic associated colitis, hepatic encephalopathy, gastric dyspepsia, cirrhosis, polycystic liver disease, pouchitis, peritonitis, inflammatory bowel disease, rosacea, sickle cell disease, *H. pylori* infection, and a combination thereof.

DETAILED DESCRIPTION

Figure 1:
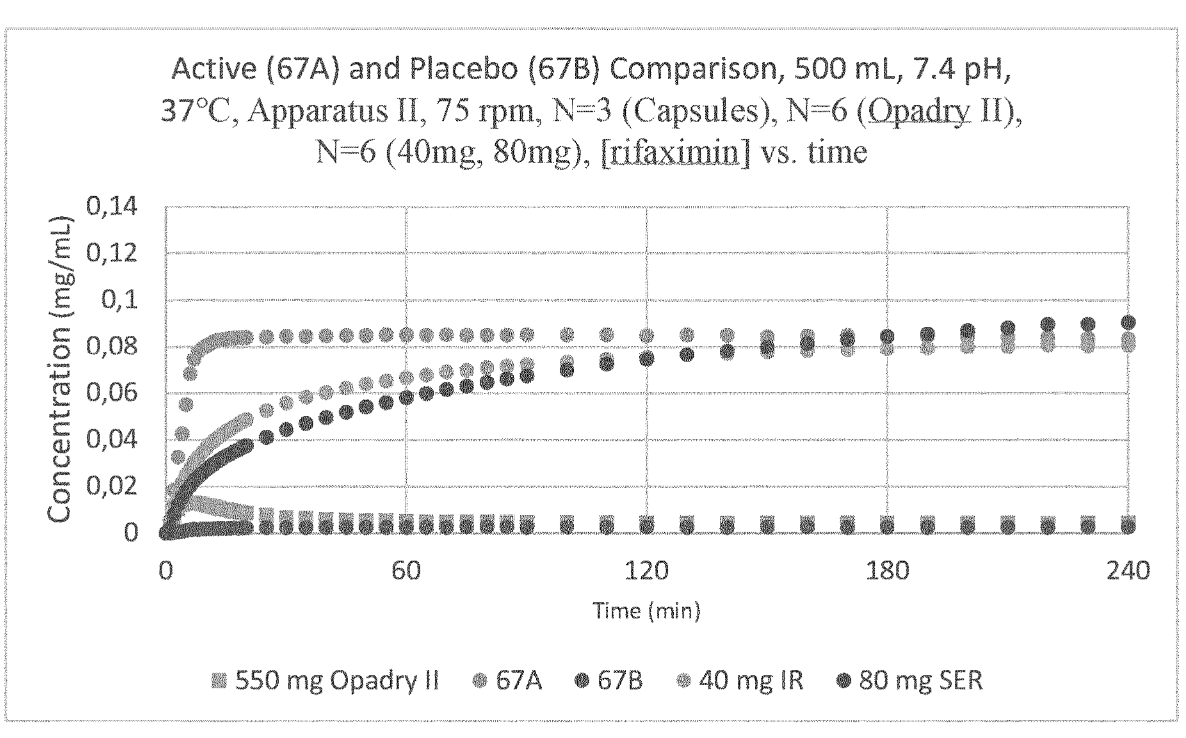
FIG. 1 shows the dissolution results for inventive composition 5425-67A compared with placebo (i.e., no rifaximin) 5425-67B, Xifaxan 550 mg (Opadry II), and 40 mg and 80 mg solid dispersion formulations as described in WO 2018/064472 (see also US Application Publication No. 2019-0224175, the entirety of which is incorporated herein by reference).

Unless defined otherwise, all technical and scientific terms used herein have the same meaning as is commonly understood by a person having ordinary skill in the art to which this invention pertains.

When ranges are used herein to describe, for example, amounts of particular compounds or ingredients, all combinations and sub-combinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The term "comprising" (and related terms such as "comprise" or "comprises" or "having" or "including") includes those embodiments such as, for example, an embodiment of any composition of matter, method or process that "consist of" or "consist essentially of" the described features.

1. Definitions

"Rifaximin" refers to the antibiotic 4-Deoxy-4'-methylpyrido[1',2'-1,2]imidazo[5,4-c]rifamycin SV, having the chemical structure depicted in Formula I:

(I)

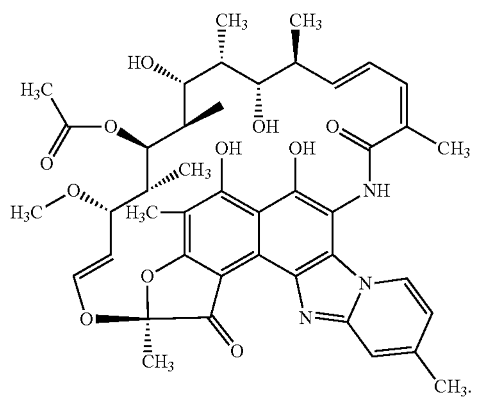

Forms, formulations, and methods of using rifaximin are described, for example, in U.S. Pat. Nos. 7,045,620, 7,906,542, 7,915,275, 8,193,196, 8,309,569, 8,518,949, 8,741,904, 9,737,610, the entirety of which are incorporated herein by reference.

The term "low dose rifaximin" means that rifaximin is present in an amount of 150 mg or less.

A "solubilizing excipient" refers to an inactive substance which is included in the disclosed compositions and which possess the ability to solubilize active pharmaceutical ingredients (APIs) such as rifaximin. Solubilizing excipients may be used, for example, e.g., in oral and injectable dosage forms. In one aspect, a "solubilizing excipient" refers to an excipient which provides for a rifaximin saturation solubility of greater than about 10% w/w. See, for example, the solubility pre-formulation procedure in the Exemplification section below. Solubilizing excipients include, but are not limited to, pH modifiers, organic solvents (e.g., water-soluble organic solvents), surfactants (e.g., non-ionic surfactants), lipids (e.g., water soluble lipids), long chain triglycerides, organic liquids/semi-solids), cyclodextrins, and phospholipids.

The term "solubilize" means to make soluble or to increase the solubility of a particular compound, such as rifaximin.

As used herein, an "antioxidant" refers to those substances which inhibit the oxidation of rifaximin, e.g., in a disclosed composition.

"Hepatic encephalopathy" or "HE" for shorthand is defined as an altered mental status diagnosed as HE and defined as an increase of the Conn score to Grade ≥2 (i.e., 0 or 1 to ≥2). HE may be considered "covert" or "overt" HE (CHE or OHE, respectively) depending upon the severity of the symptoms associated therewith. HE may be described as a continuum denoted by the West Haven Criteria (WHC): Grade 0—Minimal hepatic encephalopathy with symptoms potentially including impaired complex and sustained attention; Grade 1 (CHE)—Symptoms include trivial lack of awareness, euphoria or anxiety, shortened attention span, impairment of addition or subtraction, and altered sleep rhythm where clinical findings include mild asterixis or tremor; Grade 2 (OHE)—Symptoms include lethargy or apathy, disorientation for time, obvious personality change, and inappropriate behavior where clinical findings include obvious asterixis, dyspraxia, and slurred speech; Grade 3 (OHE)—Symptoms include somnolence to semistupor, responsive to stimuli, confused, gross disorientation, and bizarre behavior where clinical findings include muscular rigidity, clonus, and hyperreflexia; and Grade 4 (OHE)—Symptoms include coma where clinical findings include decerebrate posturing. OHE may also be observed on the Hepatic Encephalopathy Grading Instrument (HEGI), which uses clinical findings (present for at least 1 hour) to measure a patient's disorientation and thereby the severity of an HE episode (on a scale of Grade 2 to Grade 4)—Grade 4 being the most severe and Grade 2 being the least severe.

"Esophageal variceal bleeding" or "EVB" for shorthand is defined as the occurrence of a clinically significant gastrointestinal bleed being defined as 1) bleeding from an esophageal or gastric varix at the time of endoscopy or 2) the presence of large varices with blood evident in the stomach, and no other identifiable cause of bleeding observed during endoscopy, and at least one or more of the following criteria is present: i) drop in hemoglobin of greater than 2 g/dL over the first 48 hours post hospital admission, ii) transfusion requirement of 2 units of blood or more within 24 hours of hospital admission, iii) a systolic blood pressure of less than 100 mm Hg, or iv) pulse rate greater than 100 beat/min at the time of admission.

"Spontaneous bacterial peritonitis or "SBP" for shorthand is defined as greater than 250 polymorphonuclear (PMN) cells/$mm^3$ and/or positive monomicrobial culture in the ascitic fluid.

"Hepatorenal syndrome" (HRS) is defined as i) progressive rise in serum creatinine (>1.5 mg/dL) with no improvement after at least 2 days with diuretic withdrawal and volume expansion with albumin, ii) absence of parenchymal kidney disease, iii) oliguria, iv) absence of shock, and v) no current or recent (within 3 months prior randomization) treatment with nephrotoxic drugs.

The term "effective amount" or "therapeutically effective amount" refers to an amount of a composition described herein that will elicit a biological or medical response of a subject, e.g., a composition having a dosage of rifaximin between about 0.001 to about 100 mg/kg body weight/day.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

"Pharmaceutically acceptable" means molecular entities and compositions that do not produce an adverse, allergic or other untoward reaction when administered to an animal, or a human, as appropriate.

The terms "treatment," "treat," and "treating" refer to reversing, alleviating, reducing the likelihood of developing, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

2. Compositions

Disclosed herein are pharmaceutical compositions in which the intestinal levels of soluble rifaximin are significantly enhanced as compared to Xifaxan® powder. See e.g., Table 8 where over a 150-fold increase in solubility was exhibited as compared to Xifaxan® powder. As shown herein, percent of soluble rifaximin available was observed in phosphate buffer at pH 7.4. Solubility increases using the disclosed compositions were also seen in intestinal fluid. See e.g., Tables 6A and 6B. Furthermore, the effect of antioxidant additives was explored and is demonstrated in Table 7.

The solubility results and further data described herein suggest that the disclosed compositions provide means for administering lower dosages of rifaximin without compromising therapeutic efficacy. Such compositions include, for example, pharmaceutically acceptable compositions comprising rifaximin (e.g., low dose rifaximin), a hydrogenated castor oil, and at least one additional solubilizing excipient. Formulations comprising one or more of the disclosed compositions, and their use in treating bowel related or liver function disorders are also provided.

Rifaximin, a Hydrogenated Castor Oil, and at Least One Additional Solubilizing Excipient In a first embodiment, provided herein are pharmaceutically acceptable compositions comprising rifaximin, a hydrogenated castor oil, and at least one additional solubilizing excipient. Alternatively, as part of a first embodiment, the rifaximin may be a low dose rifaximin.

In a second embodiment, the hydrogenated castor oil in the disclosed compositions, e.g., as in the first embodiment, is selected from polyoxyl 8 hydrogenated castor oil, polyoxyl 10 hydrogenated castor oil, polyoxyl 16 hydrogenated castor oil, polyoxyl 20 hydrogenated castor oil, polyoxyl 25 hydrogenated castor oil, polyoxyl 35 hydrogenated castor oil, polyoxyl 40 hydrogenated castor oil (e.g., Cremophor® RH-40), polyoxyl 45 hydrogenated castor oil, polyoxyl 50 hydrogenated castor oil, polyoxyl 54 hydrogenated castor oil, polyoxyl 55 hydrogenated castor oil, polyoxyl 60 hydrogenated castor oil, polyoxyl 65 hydrogenated castor oil, polyoxyl 80 hydrogenated castor oil, polyoxyl 100 hydrogenated castor oil, and polyoxyl 200 hydrogenated castor oil, and combinations thereof. Alternatively, as part of a second embodiment, the hydrogenated castor oil in the disclosed compositions, e.g., as in the first embodiment, is polyoxyl 60 hydrogenated castor oil or polyoxyl 40 hydrogenated castor oil. In another alternative, as part of a second embodiment, the hydrogenated castor oil in the disclosed compositions, e.g., as in the first embodiment, is polyoxyl 40 hydrogenated castor oil (e.g., Cremophor® RH-40).

In a third embodiment, the hydrogenated castor oil in the disclosed compositions, e.g., as in the first embodiment or second embodiment, is present in an amount ranging from about 25% to about 65%, about 25% to about 60%, about 25% to about 55%, about 25% to about 50%, about 30% to about 45%, about 35% to about 40%, about 30% to about 40%, about 31% to about 39%, about 32% to about 38%, about 33% to about 37%, about 34% to about 36%, about 40% to about 50%, about 41% to about 49%, about 42% to about 48%, about 43% to about 47%, or about 44% to about 46%; or present in an amount of at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, or at least about 50%; or present in an amount of at most about 25%, at most about 26%, at most about 27%, at most about 28%, at most about 29%, at most about 30%, at most about 31%, at most about 32%, at most about 33%, at most about 34%, at most about 35%, at most about 36%, at most about 37%, at most about 38%, at most about 39%, at most about 40%, at most about 41%, at most about 42%, at most about 43%, at most about 44%, at most about 45%, at most about 46%, at most about 47%, at most about 48%, at most about 49%, or at most about 50%; or about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%; or present in an amount of about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%, by weight of the composition.

In an alternative third embodiment, the hydrogenated castor oil in the disclosed compositions, e.g., as in the first embodiment or second embodiment, is present in an amount ranging from about 25% to about 65%, about 25% to about 60%, about 25% to about 55%, about 25% to about 50%, about 30% to about 45%, about 35% to about 40%, about 30% to about 40%, about 31% to about 39%, about 32% to about 38%, about 33% to about 37%, about 34% to about 36%, about 40% to about 50%, about 41% to about 49%, about 42% to about 48%, about 43% to about 47%, or about 44% to about 46%; or present in an amount of at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, or at least about 50%; or present in an amount of at most about 25%, at most about 26%, at most about 27%, at most about 28%, at most about 29%, at most about 30%, at most about 31%, at most about 32%, at most about 33%, at most about 34%, at most about 35%, at most about 36%, at most about 37%, at most about 38%, at most about 39%, at most about 40%, at most about 41%, at most about 42%, at most about 43%, at most about 44%, at most about 45%, at most about 46%, at most about 47%, at most about 48%, at most about 49%, or at most about 50%; or about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%; or present in an amount of about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%, by weight of the total weight of the rifaximin, hydrogenated castor oil, and at least one additional solubilizing excipient in the composition.

In a fourth embodiment, the at least one additional solubilizing excipient in the disclosed compositions, e.g., as in any one of the first through third embodiments, is selected from a water soluble organic solvent (e.g., polyethylene glycol (e.g., PEG 300, PEG 400, and PEG 600), ethanol, propylene glycol, benzyl alcohol, oleyl alcohol, triethylene glycol, n-methyl-2-pyrrolidone, dimethylacetamide, dimethylsulfoxide, diethylene glycol monoethyl ether (e.g., Transcutol® grades HP and P), diisopropyl adipate, and diethyl sebacate), a non-ionic surfactant (e.g., PEG-8 castor oil, PEG-9 castor oil, PEG-10 castor oil, PEG-11 castor oil, PEG-15 castor oil, PEG-16 castor oil, PEG-20 castor oil, PEG-25 castor oil, PEG-26 castor oil, PEG-29 castor oil, PEG-40 castor oil, PEG-44 castor oil, PEG-50 castor oil, PEG-54 castor oil, PEG-55 castor oil, PEG-60 castor oil, PEG-75 castor oil, PEG-80 castor oil, PEG-100 castor oil, PEG-200 castor oil, polyethylene glycol 1000 succinate, polysorbate 20, polysorbate 80, poly-oxyethylene esters of 12-hydroxystearic acid, sorbitan monooleate, poloxamer 407, oleoyl macrogol-6/polyoxyl-6 glycerides, caprylocaproyl macrogol-8/polyoxyl-8 glycerides, PEG-6 caprylic/capric glycerides, lauroyl polyoxyl-32 glycerides, and mono- and di-fatty acid esters of PEG 300, PEG 400, or PEG 1750), water-insoluble lipids (e.g., castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm oil), organic liquids/semi solids (e.g., beeswax, d-α-tocopherol, oleic acid, and medium chain mono-, di-, and triglycerides (e.g., glyceryl caprylate, glyceryl monooleate, glyceryl monolinoleate, and caprylic capric triglycerides)), cyclodextrins, (e.g., α-cyclodextrin, β-cyclodextrin, and hydroxypropyl-β-cyclodextrin), and phospholipids (e.g., hydrogenated soy phosphatidylcholine).

In a fifth embodiment, the at least one additional solubilizing excipient in the disclosed compositions, e.g., as in any one of the first through fourth embodiments, is selected from a water-soluble organic solvent, a non-ionic surfactant, a water-insoluble lipid, and long-chain triglycerides, and combinations thereof. Alternatively, as part of a fourth embodiment, the at least one additional solubilizing excipient in the disclosed compositions, e.g., as in any one of the first through fourth embodiments, is selected from polyethylene glycol 600, glyceryl caprylate, polysorbate 80, castor oil, benzyl alcohol, polyethylene glycol 400, diethylene glycol monoethyl ether, glyceryl monooleate, triethylene glycol, diisopropyl adipate, diethyl sebacate, oleyl alcohol, polysorbate 20, oleic acid, caprylic capric triglycerides, propylene glycol, sesame oil, soybean oil, and corn oil, and combinations thereof.

In a sixth embodiment, the at least one additional solubilizing excipient in the disclosed compositions, e.g., as in any one of the first through fifth embodiments, is one which allows for a rifaximin saturation solubility of greater than about 10% w/w (e.g., greater than about 11% w/w, greater than about 12% w/w, greater than about 13% w/w, greater than about 14% w/w, greater than about 15% w/w, greater than about 16% w/w, greater than about 17% w/w, greater than about 18% w/w, greater than about 19% w/w, or greater than about 20% w/w). Alternatively, as part of a sixth embodiment, the at least one additional solubilizing excipient in the disclosed compositions, e.g., as in any one of the first through fifth embodiments, is one which allows for a rifaximin saturation solubility of from about 10% w/w to about 25% w/w, from about 12% w/w to about 25% w/w, from about 12% w/w to about 23% w/w, from about 13% w/w to about 23% w/w, or from about 14% w/w to about 22% w/w.

In a seventh embodiment, the at least one additional solubilizing excipient in the disclosed compositions, e.g., as in any one of the first through sixth embodiments, is selected from polyethylene glycol 600, glyceryl caprylate, polysorbate 80, castor oil, benzyl alcohol, polyethylene glycol 400, diethylene glycol monoethyl ether, glyceryl monooleate, triethylene glycol, diisopropyl adipate, diethyl sebacate, oleyl alcohol, and combinations thereof. Alternatively, as part of a seventh embodiment, the at least one additional solubilizing excipient in the disclosed compositions, e.g., as in any one of the first through sixth embodiments, is selected from castor oil, glyceryl caprylate, polysorbate 80, diethyl sebacate, and diethylene glycol monoethyl ether, and combinations thereof.

In an eighth embodiment, the at least one additional solubilizing excipient in the disclosed compositions, e.g., as in any one of the first through seventh embodiments, is present in an amount ranging from about 25% to about 70%, about 25% to about 65%, about 30% to about 65%, about 35% to about 65%, about 40% to about 65%, about 40% to about 70%, about 45% to about 65%, about 46% to about 65%, about 47% to about 65%, about 48% to about 65%, about 49% to about 65%, about 50% to about 65%, about 45% to about 60%, about 46% to about 60%, about 47% to about 60%, about 48% to about 60%, about 49% to about 60%, about 50% to about 60%, about 51% to about 60%, about 52% to about 60%, about 53% to about 60%, about 54% to about 60%, or about 55% to about 60%; or present in an amount of at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, or at least about 70%; or present in an amount of at most about 25%, at most about 26%, at most about 27%, at most about 28%, at most about 29%, at most about 30%, at most about 31%, at most about 32%, at most about 33%, at most about 34%, at most about 35%, at most about 36%, at most about 37%, at most about 38%, at most about 39%, at most about 40%, at most about 41%, at most about 42%, at most about 43%, at most about 44%, at most about 45%, at most about 46%, at most about 47%, at most about 48%, at most about 49%, at most about 50%, at most about 51%, at most about 52%, at most about 53%, at most about 54%, at most about 55%, at most about 56%, at most about 57%, at most about 58%, at most about 59%, at most about 60%, at most about 61%, at most about 62%, at most about 63%, at most about 64%, at most about 65%, at most about 66%, at most about 67%, at most about 68%, at most about 69%, or at most about 70%; or present in an amount of about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, or about 70%, by weight of the composition. Alternatively, as part of an eighth embodiment, the at least one additional solubilizing excipient in the disclosed compositions, e.g., as in any one of the first through seventh embodiments, is present in an amount ranging from about 51% to about 59%, about 52% to about 58%, about 53% to about 57%, or about 54% to about 56% by weight of the composition. Alternatively, as part of an eighth embodiment, the at least one additional solubilizing excipient in the disclosed compositions, e.g., as in any one of the first through seventh embodiments, is present in an amount ranging from about 59% to about 66%, about 60% to about 65%, about 61% to about 64%, or about 62% to about 63% by weight of the composition.

In an alternative eighth embodiment, the at least one additional solubilizing excipient in the disclosed compositions, e.g., as in any one of the first through seventh embodiments, is present in an amount ranging from about 40% to about 70%, about 45% to about 65%, about 46% to about 65%, about 47% to about 65%, about 48% to about 65%, about 49% to about 65%, about 50% to about 65%, about 45% to about 60%, about 46% to about 60%, about 47% to about 60%, about 48% to about 60%, about 49% to about 60%, about 50% to about 60%, about 51% to about 60%, about 52% to about 60%, about 53% to about 60%, about 54% to about 60%, about 55% to about 65%, about 62% to about 63%, or about 55% to about 60%; or present in an amount of at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, or at least about 70%; or present in an amount of at most about 40%, at most about 41%, at most about 42%, at most about 43%, at most about 44%, at most about 45%, at most about 46%, at most about 47%, at most about 48%, at most about 49%, at most about 50%, at most about 51%, at most about 52%, at most about 53%, at most about 54%, at most about 55%, at most about 56%, at most about 57%, at most about 58%, at most about 59%, at most about 60%, at most about 61%, at most about 62%, at most about 63%, at most about 64%, at most about 65%, at most about 66%, at most about 67%, at most about 68%, at most about 69%, or at most about 70%; or present in an amount of about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, or about 70%, by weight of the total weight of the rifaximin, hydrogenated castor oil, and at least one additional solubilizing excipient the composition. Alternatively, as part of an eighth embodiment, the at least one additional solubilizing excipient in the disclosed compositions, e.g., as in any one of the first through seventh embodiments, is present in an amount ranging from about 51% to about 59%, about 52% to about 58%, about 53% to about 57%, or about 54% to about 56% by weight of the total weight of the rifaximin, hydrogenated castor oil, and at least one additional solubilizing excipient in the composition.

In some embodiments of any one of the first through eighth embodiments, the hydrogenated castor oil and at least one additional solubilizing excipient may be provided in a ratio of about 1:3 and about 1.5:1, respectively, by weight hydrogenated castor oil and at least one additional solubilizing excipient. In some embodiments of any one of the first through eighth embodiments, the hydrogenated castor oil and at least one additional solubilizing excipient may be provided in a ratio of about 1:3 to about 1.5:1, respectively, by weight hydrogenated castor oil and at least one additional solubilizing excipient.

In some embodiments of any one of the first through eighth embodiments, the hydrogenated castor oil and at least one additional solubilizing excipient may be provided in a ratio of about 1:1 and about 1:2.5, respectively, by weight hydrogenated castor oil and at least one additional solubilizing excipient. In some embodiments of any one of the first through eighth embodiments, the hydrogenated castor oil and at least one additional solubilizing excipient may be provided in a ratio of about 1:1 to about 1:2.5, respectively, by weight hydrogenated castor oil and at least one additional solubilizing excipient.

Rifaximin, a Hydrogenated Castor Oil, Castor Oil, Glyceryl Caprylate, and Polysorbate 80

In a ninth embodiment, the at least one additional solubilizing excipient in the disclosed compositions, e.g., as in any one of the first through eighth embodiments, is a combination of castor oil, glyceryl caprylate, and polysorbate 80.

In a tenth embodiment, the at least one additional solubilizing excipient in the disclosed compositions, e.g., as in any one of the first through ninth embodiments, is a combination of castor oil, glyceryl caprylate, and polysorbate 80, wherein:

the castor oil is present in an amount ranging from about 5% to about 15%, or about 6% to about 14%, or about 7% to about 13%, or about 8% to about 12%, or about 9% to about 11%; or present in an amount of at least about 5%, at least about 6%, at least about 7%, at least about 8%, at least about 9%, at least about 10%, at least about 11%, at least about 12%, at least about 13%, at least about 14%, or at least about 15%; or present in an amount of at most about 5%, at most about 6%, at most about 7%, at most about 8%, at most about 9%, at most about 10%, at most about 11%, at most about 12%, at most about 13%, at most about 14%, or at most about 15%; or present in an amount of about 5%, about 6%, about 7%, about 8%, about 9%, about 10%, about 11%, about 12%, about 13%, about 14%, or about 15%, by weight of the composition;

the glyceryl caprylate is present in an amount ranging from about 5% to about 15%, or about 10% to about 15%, or about 38% to about 42%, or about 6% to about 14%, or about 7% to about 13%, or about 8% to about 12%, or about 9% to about 11%; or present in an amount of at least about 5%, at least about 6%, at least about 7%, at least about 8%, at least about 9%, at least about 10%, at least about 11%, at least about 12%, at least about 13%, at least about 14%, or at least about 15%; or present in an amount of at most about 5%, at most about 6%, at most about 7%, at most about 8%, at most about 9%, at most about 10%, at most about 11%, at most about 12%, at most about 13%, at most about 14%, or at most about 15%; or present in an amount of about 5%, about 6%, about 7%, about 8%, about 9%, about 10%, about 11%, about 12%, about 13%, about 14%, or about 15%, by weight of the composition; and the polysorbate 80 is present in an amount ranging from about 20% to about 40%, 35% to about 45%, or about 25% to about 40%, or about 27% to about 40%, or about 25% to about 37%, or about 27% to about 37%, or about 28% to about 36%, or about 30% to about 35%, or about 32% to about 35%; or present in an amount of at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, or at least about 40%; or present in an amount of at most about 25%, at most about 26%, at most about 27%, at most about 28%, at most about 29%, at most about 30%, at most about 31%, at most about 32%, at most about 33%, at most about 34%, at most about 35%, at most about 36%, at most about 37%, at most about 38%, at most about 39%, or at most about 40%; or present in an amount of about 25%, about 26%, about 27%, about 28%, about 29%, about 30%, about 31%, about 32%, about 33%, about 34%, about 35%, about 36%, about 37%, about 38%, about 39%, or about 40%, by weight of the composition.

Alternatively, as part of a tenth embodiment, the at least one additional solubilizing excipient in the disclosed compositions, e.g., as in any one of the first through ninth embodiments, is a combination of castor oil, glyceryl caprylate, and polysorbate 80, wherein the castor oil is present in an amount ranging from about 8% to about 12% by weight of the composition; the glyceryl caprylate is present in an amount ranging from about 10% to about 14% by weight of the composition; and the polysorbate 80 is present in an amount ranging from about 30% to about 35% by weight of the composition. In another alternative, as part of a tenth embodiment, the at least one additional solubilizing excipient in the disclosed compositions, e.g., as in any one of the first through ninth embodiments, is a combination of castor oil, glyceryl caprylate, and polysorbate 80, wherein:

the castor oil is present in an amount ranging from about 10% to about 20% (e.g., about 11% to about 19%, about 12% to about 18%, about 13% to about 17%, or about 14% to about 16%), or present in an amount of at least about 10%, at least about 11%, at least about 12%, at least about 13%, at least about 14%, at least about 15%, at least about 16%, at least about 17%, at least about 18%, at least about 19%, or at least about 20%, or present in an amount of at most about 10%, at most about 11%, at most about 12%, at most about 13%, at most about 14%, at most about 15%, at most about 16%, at most about 17%, at most about 18%, at most about 19%, or at most about 20%, or present in an amount of about 10%, about 11%, about 12%, about 13%, about 14%, about 15%, about 16%, about 17%, about 18%, about 19%, or about 20%, by weight of the composition;

the glyceryl caprylate is present in an amount ranging from about 5% to about 15% (e.g., about 6% to about 14%, about 7% to about 13%, about 8% to about 12%, or about 9% to about 11%), or present in an amount of at least about 5%, at least about 6%, at least about 7%, at least about 8%, at least about 9%, at least about 10%, at least about 11%, at least about 12%, at least about 13%, at least about 14%, or at least about 15%, or present in an amount of at most about 5%, at most about 6%, at most about 7%, at most about 8%, at most about 9%, at most about 10%, at most about 11%, at most about 12%, at most about 13%, at most about 14%, or at most about 15%, or present in an amount of about 5%, about 6%, about 7%, about 8%, about 9%, about 10%, about 11%, about 12%, about 13%, about 14%, or about 15%, by weight of the composition; and the polysorbate 80 is present in an amount ranging from about 20% to about 40% (e.g., about 25% to about 40%, about 27% to about 40%, about 25% to about 37%, about 27% to about 37%, about 28% to about 36%, about 30% to about 35%, or about 32% to about 35%), or present in an amount of at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, or at least about 40%, or present in an amount of at most about 20%, at most about 21%, at most about 22%, at most about 23%, at most about 24%, at most about 25%, at most about 26%, at most about 27%, at most about 28%, at most about 29%, at most about 30%, at most about 31%, at most about 32%, at most about 33%, at most about 34%, at most about 35%, at most about 36%, at most about 37%, at most about 38%, at most about 39%, or at most about 40%, or present in an amount of about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40%, by weight of the composition.

In another alternative, as part of a tenth embodiment, the at least one additional solubilizing excipient in the disclosed compositions, e.g., as in any one of the first through ninth embodiments, is a combination of castor oil, glyceryl caprylate, and polysorbate 80, wherein the castor oil is present in an amount ranging from about 13% to about 18% by weight of the composition; the glyceryl caprylate is present in an amount ranging from about 10% to about 14% by weight of the composition; and the polysorbate 80 is present in an amount ranging from about 30% to about 35% by weight of the composition.

In an alternative tenth embodiment, the at least one additional solubilizing excipient in the disclosed compositions, e.g., as in any one of the first through ninth embodiments, is a combination of castor oil, glyceryl caprylate, and polysorbate 80, wherein:

the castor oil is present in an amount ranging from about 5% to about 15%, or about 6% to about 14%, or about 7% to about 13%, or about 8% to about 12%, or about 9% to about 11%; or present in an amount of at least about 5%, at least about 6%, at least about 7%, at least about 8%, at least about 9%, at least about 10%, at least about 11%, at least about 12%, at least about 13%, at least about 14%, or at least about 15%; or present in an amount of at most about 5%, at most about 6%, at most about 7%, at most about 8%, at most about 9%, at most about 10%, at most about 11%, at most about 12%, at most about 13%, at most about 14%, or at most about 15%; or present in an amount of about 5%, about 6%, about 7%, about 8%, about 9%, about 10%, about 11%, about 12%, about 13%, about 14%, or about 15%, by weight of the total weight of the rifaximin, hydrogenated castor oil, glyceryl caprylate, and polysorbate 80;

the glyceryl caprylate is present in an amount ranging from about 5% to about 15%, or about 6% to about 14%, or about 7% to about 13%, or about 8% to about 12%, or about 9% to about 11%; or present in an amount of at least about 5%, at least about 6%, at least about 7%, at least about 8%, at least about 9%, at least about 10%, at least about 11%, at least about 12%, at least about 13%, at least about 14%, or at least about 15%; or present in an amount of at most about 5%, at most about 6%, at most about 7%, at most about 8%, at most about 9%, at most about 10%, at most about 11%, at most about 12%, at most about 13%, at most about 14%, or at most about 15%; or present in an amount of about 5%, about 6%, about 7%, about 8%, about 9%, about 10%, about 11%, about 12%, about 13%, about 14%, or about 15%, by weight of the total weight of the rifaximin, hydrogenated castor oil, glyceryl caprylate, and polysorbate 80; and the polysorbate 80 is present in an amount ranging from about 20% to about 40%, or about 25% to about 40%, or about 27% to about 40%, or about 25% to about 37%, or about 27% to about 37%, or about 28% to about 36%, or about 30% to about 35%, or about 32% to about 35%; or present in an amount of at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, or at least about 40%; or present in an amount of at most about 25%, at most about 26%, at most about 27%, at most about 28%, at most about 29%, at most about 30%, at most about 31%, at most about 32%, at most about 33%, at most about 34%, at most about 35%, at most about 36%, at most about 37%, at most about 38%, at most about 39%, or at most about 40%; or present in an amount of about 25%, about 26%, about 27%, about 28%, about 29%, about 30%, about 31%, about 32%, about 33%, about 34%, about 35%, about 36%, about 37%, about 38%, about 39%, or about 40%, by weight of the total weight of the rifaximin, hydrogenated castor oil, glyceryl caprylate, and polysorbate 80.

Alternatively, as part of a tenth embodiment, the at least one additional solubilizing excipient in the disclosed compositions, e.g., as in any one of the first through ninth embodiments, is a combination of castor oil, glyceryl caprylate, and polysorbate 80, wherein the castor oil is present in an amount ranging from about 8% to about 12% by weight of the total weight of the rifaximin, hydrogenated castor oil, glyceryl caprylate, and polysorbate 80; the glyceryl caprylate is present in an amount ranging from about 10% to about 14% by weight of the total weight of the rifaximin, hydrogenated castor oil, glyceryl caprylate, and polysorbate 80; and the polysorbate 80 is present in an amount ranging from about 30% to about 35% by weight of the total weight of the rifaximin, hydrogenated castor oil, glyceryl caprylate, and polysorbate 80. In another alternative, as part of a tenth embodiment, the at least one additional solubilizing excipient in the disclosed compositions, e.g., as in any one of the first through ninth embodiments, is a combination of castor oil, glyceryl caprylate, and polysorbate 80, wherein:

the castor oil is present in an amount ranging from about 10% to about 20% (e.g., about 11% to about 19%, about 12% to about 18%, about 13% to about 17%, or about 14% to about 16%), or present in an amount of at least about 10%, 11%, 12%, 13%, 14%, 15%, 16%, 17%, 18%, 19%, or 20%, or present in an amount of at most about 10%, 11%, 12%, 13%, 14%, 15%, 16%, 17%, 18%, 19%, or 20%, or present in an amount of about 10%, 11%, 12%, 13%, 14%, 15%, 16%, 17%, 18%, 19%, or 20%, by weight of the total weight of the rifaximin, hydrogenated castor oil, glyceryl caprylate, and polysorbate 80;

the glyceryl caprylate is present in an amount ranging from about 5% to about 15% (e.g., about 6% to about 14%, about 7% to about 13%, about 8% to about 12%, or about 9% to about 11%), or present in an amount of at least about 5%, at least about 6%, at least about 7%, at least about 8%, at least about 9%, at least about 10%, at least about 11%, at least about 12%, at least about 13%, at least about 14%, or at least about 15%, or present in an amount of at most about at most about 5%, at most about 6%, at most about 7%, at most about 8%, at most about 9%, at most about 10%, at most about 11%, at most about 12%, at most about 13%, at most about 14%, or at most about 15%, or present in an amount of about 5%, about 6%, about 7%, about 8%, about 9%, about 10%, about 11%, about 12%, about 13%, about 14%, or about 15%, by weight of the total weight of the rifaximin, hydrogenated castor oil, glyceryl caprylate, and polysorbate 80; and the polysorbate 80 is present in an amount ranging from about 20% to about 40% (e.g., about 25% to about 40%, about 27% to about 40%, about 25% to about 37%, about 27% to about 37%, about 28% to about 36%, about 30% to about 35%, or about 32% to about 35%), or present in an amount of at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, or at least about 40%, or present in an amount of at most about 20%, at most about 21%, at most about 22%, at most about 23%, at most about 24%, at most about 25%, at most about 26%, at most about 27%, at most about 28%, at most about 29%, at most about 30%, at most about 31%, at most about 32%, at most about 33%, at most about 34%, at most about 35%, at most about 36%, at most about 37%, at most about 38%, at most about 39%, or at most about 40%, or present in an amount of about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40%, by weight of the total weight of the rifaximin, hydrogenated castor oil, glyceryl caprylate, and polysorbate 80.

In another alternative, as part of a tenth embodiment, the at least one additional solubilizing excipient in the disclosed compositions, e.g., as in any one of the first through ninth embodiments, is a combination of castor oil, glyceryl caprylate, and polysorbate 80, wherein the castor oil is present in an amount ranging from about 13% to about 18% by weight of the total weight of the rifaximin, hydrogenated castor oil, glyceryl caprylate, and polysorbate 80; the glyceryl caprylate is present in an amount ranging from about 10% to about 14% by weight of the composition; and the polysorbate 80 is present in an amount ranging from about 30% to about 35% by weight of the total weight of the rifaximin, hydrogenated castor oil, glyceryl caprylate, and polysorbate 80.

In another alternative, as part of a tenth embodiment, the at least one additional solubilizing excipient in the disclosed compositions, e.g., as in any one of the first through ninth embodiments, is a combination of castor oil, glyceryl caprylate, and polysorbate 80, wherein the castor oil is present in an amount ranging from about 5% to about 15% by weight of the composition; the glyceryl caprylate is present in an amount ranging from about 10% to about 15% by weight of the composition; and the polysorbate 80 is present in an amount ranging from about 35% to about 45% by weight of the composition.

In another alternative, as part of a tenth embodiment, the at least one additional solubilizing excipient in the disclosed compositions, e.g., as in any one of the first through ninth embodiments, is a combination of castor oil, glyceryl caprylate, and polysorbate 80, wherein the castor oil is present in an amount ranging from about 8% to about 12% by weight of the composition; the glyceryl caprylate is present in an amount ranging from about 10% to about 15% by weight of the composition; and the polysorbate 80 is present in an amount ranging from about 38% to about 42% by weight of the composition.

Rifaximin, a Hydrogenated Castor Oil, Diethyl Sebacate, and Diethylene Glycol Monoethyl Ether In an eleventh embodiment, the at least one additional solubilizing excipient in the disclosed compositions, e.g., as in any one of the first through eighth embodiments, is a combination of diethyl sebacate and diethylene glycol monoethyl ether. Alternatively, as part of an eleventh embodiment, the diethylene glycol monoethyl ether is diethylene glycol monoethyl ether.

In a twelfth embodiment, the at least one additional solubilizing excipient in the disclosed compositions, e.g., as in any one of the first through eighth and eleventh embodiments, is a combination of diethyl sebacate and diethylene glycol monoethyl ether, wherein:

the diethyl sebacate is present in an amount ranging from about 20% to about 35%, or about 21% to about 34%, or about 22% to about 33%, or about 23% to about 32%, or about 24% to about 31%, or about 25% to about 30%, or about 26% to about 29%, or about 26% to about 38%, or about 27% to about 28%, or present in amount of at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, or at least about 35%, or present in an amount of at most about 20%, at most about 21%, at most about 22%, at most about 23%, at most about 24%, at most about 25%, at most about 26%, at most about 27%, at most about 28%, at most about 29%, at most about 30%, at most about 31%, at most about 32%, at most about 33%, at most about 34%, or at most about 35%, or present in an amount of about 20%, about 21%, about 22%, about 23%, about 24%, about 25%, about 26%, about 27%, about 28%, about 29%, about 30%, about 31%, about 32%, about 33%, about 34%, or about 35%, by weight of the composition; and the diethylene glycol monoethyl ether is present in an amount ranging from about 20% to about 35%, or about 21% to about 34%, or about 22% to about 33%, or about 23% to about 32%, or about 24% to about 31%, or about 25% to about 30%, or about 26% to about 29%, or about 26% to about 38%, or about 27% to about 28%, or present in amount of at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, or at least about 35%, or present in an amount of at most about 20%, at most about 21%, at most about 22%, at most about 23%, at most about 24%, at most about 25%, at most about 26%, at most about 27%, at most about 28%, at most about 29%, at most about 30%, at most about 31%, at most about 32%, at most about 33%, at most about 34%, or at most about 35%, or present in an amount of about 20%, about 21%, about 22%, about 23%, about 24%, about 25%, about 26%, about 27%, about 28%, about 29%, about 30%, about 31%, about 32%, about 33%, about 34%, or about 35%, by weight of the composition.

Alternatively, as part of a twelfth embodiment, the at least one additional solubilizing excipient in the disclosed compositions, e.g., as in any one of the first through eighth and eleventh embodiments, is a combination of diethyl sebacate and diethylene glycol monoethyl ether, wherein the diethyl sebacate is present in an amount ranging from about 25% to about 30% by weight of the composition; and the diethylene glycol monoethyl ether is present in an amount ranging from about 25% to about 30% by weight of the composition. In another alternative, as part of a twelfth embodiment, the at least one additional solubilizing excipient in the disclosed compositions, e.g., as in any one of the first through eighth and eleventh embodiments, is a combination of diethyl sebacate and diethylene glycol monoethyl ether, wherein:

the diethyl sebacate is present in an amount ranging from about 10% to about 20%, or about 11% to about 19%, or about 12% to about 18%, or about 13% to about 18%, or about 14% to about 18%, or about 15% to about 18%, or about 16% to about 18%, or about 16% to about 17%, or present in an amount of at least about 10%, at least about 11%, at least about 12%, at least about 13%, at least about 14%, at least about 15%, at least about 16%, at least about 17%, at least about 18%, at least about 19%, or at least about 20%, or present in an amount of at most about 10%, at most about 11%, at most about 12%, at most about 13%, at most about 14%, at most about 15%, at most about 16%, at most about 17%, at most about 18%, at most about 19%, or at most about 20%, or present in an amount of about 10%, about 11%, about 12%, about 13%, about 14%, about 15%, about 16%, about 17%, about 18%, about 19%, or about 20%, by weight of the composition; and the diethylene glycol monoethyl ether is present in an amount ranging from about 30% to about 45%, or about 31% to about 44%, or about 32% to about 43%, or about 33% to about 42%, or about 34% to about 41%, or about 35% to about 40%, or about 36% to about 49%, or about 37% to about 49%, or present in an amount of at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, or at least about 45%, or present in an amount of at most about 30%, at most about 31%, at most about 32%, at most about 33%, at most about 34%, at most about 35%, at most about 36%, at most about 37%, at most about 38%, at most about 39%, at most about 40%, at most about 41%, at most about 42%, at most about 43%, at most about 44%, or at most about 45%, or present in an amount of about 30%, about 31%, about 32%, about 33%, about 34%, about 35%, about 36%, about 37%, about 38%, about 39%, about 40%, about 41%, about 42%, about 43%, about 44%, or about 45%, by weight of the composition.

In another alternative, as part of a twelfth embodiment, the at least one additional solubilizing excipient in the disclosed compositions, e.g., as in any one of the first through eighth and eleventh embodiments, is a combination of diethyl sebacate and diethylene glycol monoethyl ether, wherein the diethyl sebacate is present in an amount ranging from about 14% to about 18% by weight of the composition; and the diethylene glycol monoethyl ether is present in an amount ranging from about 36% to about 40% by weight of the composition.

In an alternative twelfth embodiment, the at least one additional solubilizing excipient in the disclosed compositions, e.g., as in any one of the first through eighth and eleventh embodiments, is a combination of diethyl sebacate and diethylene glycol monoethyl ether, wherein:

the diethyl sebacate is present in an amount ranging from about 20% to about 35%, or about 21% to about 34%, or about 22% to about 33%, or about 23% to about 32%, or about 24% to about 31%, or about 25% to about 30%, or about 26% to about 29%, or about 26% to about 38%, or about 27% to about 28%, or present in amount of at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, or at least about 35%, or present in an amount of at most about 20%, at most about 21%, at most about 22%, at most about 23%, at most about 24%, at most about 25%, at most about 26%, at most about 27%, at most about 28%, at most about 29%, at most about 30%, at most about 31%, at most about 32%, at most about 33%, at most about 34%, or at most about 35%, or present in an amount of about 20%, about 21%, about 22%, about 23%, about 24%, about 25%, about 26%, about 27%, about 28%, about 29%, about 30%, about 31%, about 32%, about 33%, about 34%, or about 35%, by weight of the total weight of the rifaximin, hydrogenated castor oil, diethyl sebacate, and diethylene glycol monoethyl ether; and the diethylene glycol monoethyl ether is present in an amount ranging from about 20% to about 35%, or about 21% to about 34%, or about 22% to about 33%, or about 23% to about 32%, or about 24% to about 31%, or about 25% to about 30%, or about 26% to about 29%, or about 26% to about 38%, or about 27% to about 28%, or present in amount of at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, or at least about 35%, or present in an amount of at most about 20%, at most about 21%, at most about 22%, at most about 23%, at most about 24%, at most about 25%, at most about 26%, at most about 27%, at most about 28%, at most about 29%, at most about 30%, at most about 31%, at most about 32%, at most about 33%, at most about 34%, or at most about 35%, or present in an amount of about 20%, about 21%, about 22%, about 23%, about 24%, about 25%, about 26%, about 27%, about 28%, about 29%, about 30%, about 31%, about 32%, about 33%, about 34%, or about 35%, by weight of the total weight of the rifaximin, hydrogenated castor oil, diethyl sebacate, and diethylene glycol monoethyl ether. Alternatively, as part of a twelfth embodiment, the at least one additional solubilizing excipient in the disclosed compositions, e.g., as in any one of the first through eighth and eleventh embodiments, is a combination of diethyl sebacate and diethylene glycol monoethyl ether, wherein the diethyl sebacate is present in an amount ranging from about 25% to about 30% by weight of the total weight of the rifaximin, hydrogenated castor oil, diethyl sebacate, and diethylene glycol monoethyl ether; and the diethylene glycol monoethyl ether is present in an amount ranging from about 25% to about 30% by weight of the total weight of the rifaximin, hydrogenated castor oil, diethyl sebacate, and diethylene glycol monoethyl ether. In another alternative, as part of a twelfth embodiment, the at least one additional solubilizing excipient in the disclosed compositions, e.g., as in any one of the first through eighth and eleventh embodiments, is a combination of diethyl sebacate and diethylene glycol monoethyl ether, wherein:

the diethyl sebacate is present in an amount ranging from about 10% to about 20%, or about 11% to about 19%, or about 12% to about 18%, or about 13% to about 18%, or about 14% to about 18%, or about 15% to about 18%, or about 16% to about 18%, or about 16% to about 17%, or present in an amount of at least about 10%, at least about 11%, at least about 12%, at least about 13%, at least about 14%, at least about 15%, at least about 16%, at least about 17%, at least about 18%, at least about 19%, or at least about 20%, or present in an amount of at most about 10%, at most about 11%, at most about 12%, at most about 13%, at most about 14%, at most about 15%, at most about 16%, at most about 17%, at most about 18%, at most about 19%, or at most about 20%, or present in an amount of about 10%, about 11%, about 12%, about 13%, about 14%, about 15%, about 16%, about 17%, about 18%, about 19%, or about 20%, by weight of the total weight of the rifaximin, hydrogenated castor oil, diethyl sebacate, and diethylene glycol monoethyl ether; and the diethylene glycol monoethyl ether is present in an amount ranging from about 30% to about 45%, or about 31% to about 44%, or about 32% to about 43%, or about 33% to about 42%, or about 34% to about 41%, or about 35% to about 40%, or about 36% to about 49%, or about 37% to about 49%, or present in an amount of at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, or at least about 45%, or present in an amount of at most about 30%, at most about 31%, at most about 32%, at most about 33%, at most about 34%, at most about 35%, at most about 36%, at most about 37%, at most about 38%, at most about 39%, at most about 40%, at most about 41%, at most about 42%, at most about 43%, at most about 44%, or at most about 45%, or present in an amount of about 30%, about 31%, about 32%, about 33%, about 34%, about 35%, about 36%, about 37%, about 38%, about 39%, about 40%, about 41%, about 42%, about 43%, about 44%, or about 45%, by weight of the total weight of the rifaximin, hydrogenated castor oil, diethyl sebacate, and diethylene glycol monoethyl ether.

In another alternative, as part of a twelfth embodiment, the at least one additional solubilizing excipient in the disclosed compositions, e.g., as in any one of the first through eighth and eleventh embodiments, is a combination of diethyl sebacate and diethylene glycol monoethyl ether, wherein the diethyl sebacate is present in an amount ranging from about 14% to about 18% by weight of the total weight of the rifaximin, hydrogenated castor oil, diethyl sebacate, and diethylene glycol monoethyl ether; and the diethylene glycol monoethyl ether is present in an amount ranging from about 36% to about 40% by weight of the total weight of the rifaximin, hydrogenated castor oil, diethyl sebacate, and diethylene glycol monoethyl ether.

Antioxidants/Chelating Agents

In a thirteenth embodiment, the compositions described herein e.g., as in any one of the first through twelfth embodiments further comprise an antioxidant and/or a chelating agent.

In a fourteenth embodiment, the compositions described herein e.g., as in any one of the first through thirteenth embodiments further comprise an antioxidant and/or chelating agent selected from ascorbyl palmitate, butylated hydroxyanisole, butylated hydroxytoluene (BHT), citric acid, sodium metabisulfite, cysteine, potassium metabisulfite, propyl gallate, sodium thiosulfate, vitamin E, and 3,4-dihydroxybenzoic acid. Without being limited to any one theory of the invention, BHT and citric acid, for example, may be used as antioxidants and/or chelating agents to minimize potential degradation of rifaximin via oxidation.

Alternatively, as part of a fourteenth embodiment, the compositions described herein e.g., as in any one of the first through thirteenth embodiments further comprise BHT. In another alternative, as part of a fourteenth embodiment, the compositions described herein e.g., as in any one of the first through thirteenth embodiments further comprise BHT in an amount of less than about 1% (e.g., less than about 0.5%, less than about 0.1%, less than about 0.08%, less than about 0.06%, less than about 0.04%) by weight of the composition.

In another alternative, as part of a fourteenth embodiment, the compositions described herein e.g., as in any one of the first through thirteenth embodiments further comprise BHT in an amount ranging from about 0.01% to about 0.1%, from about 0.02% to about 0.08%, from about 0.025% to about 0.06%, from about 0.03% to about 0.06%, from about 0.03% to about 0.05%, from about 0.05% to about 0.15%, or from about 0.03% to about 0.04% by weight of the composition.

Alternatively, as part of a fourteenth embodiment, the compositions described herein e.g., as in any one of the first through thirteenth embodiments further comprise citric acid. In another alternative, as part of a fourteenth embodiment, the compositions described herein e.g., as in any one of the first through thirteenth embodiments further comprise citric acid in an amount of less than about 1% (e.g., less than about 0.5%, less than about 0.1%, less than about 0.08%, less than about 0.06%, less than about 0.04%) by weight of the composition.

In another alternative, as part of a fourteenth embodiment, the compositions described herein e.g., as in any one of the first through thirteenth embodiments further comprise citric acid in an amount ranging from about 0.01% to about 0.1%, from about 0.02% to about 0.08%, from about 0.025% to about 0.06%, from about 0.03% to about 0.06%, from about 0.03% to about 0.05%, or from about 0.03% to about 0.04% by weight of the composition.

Alternatively, as part of a fourteenth embodiment, the compositions described herein e.g., as in any one of the first through thirteenth embodiments further comprise ascorbyl palmitate. Alternatively, as part of a fourteenth embodiment, the compositions described herein e.g., as in any one of the first through thirteenth embodiments further comprise ascorbyl palmitate in an amount ranging from about 0.05% to about 0.15%, from about 0.06% to about 0.14%, from about 0.07% to about 0.13%, from about 0.08% to about 0.12%, or from about 0.08% to about 0.12% by weight of the composition.

Alternatively, as part of a fourteenth embodiment, the compositions described herein e.g., as in any one of the first through thirteenth embodiments further comprise BHT and citric acid. In another alternative, as part of a fourteenth embodiment, the compositions described herein e.g., as in any one of the first through thirteenth embodiments further comprise BHT and citric acid each in an amount of less than about 1% (e.g., less than about 0.5%, less than about 0.1%, less than about 0.08%, less than about 0.06%, less than about 0.04%) by weight of the composition.

In another alternative, as part of a fourteenth embodiment, the compositions described herein e.g., as in any one of the first through thirteenth embodiments further comprise BHT and citric acid each in an amount ranging from about 0.01% to about 0.1%, from about 0.02% to about 0.08%, from about 0.025% to about 0.06%, from about 0.03% to about 0.06%, from about 0.03% to about 0.05%, or from about 0.03% to about 0.04% by weight of the composition.

In another alternative, as part of a fourteenth embodiment, the compositions described herein e.g., as in any one of the first through thirteenth embodiments further comprise BHT, citric acid, and ascorbyl palmitate each in an amount ranging from about 0.05% to about 0.15%, from about 0.06% to about 0.14%, from about 0.7% to about 0.13%, from about 0.8% to about 0.12%, or from about 0.09% to about 0.11%, by weight of the composition.

Rifaximin

In a fifteenth embodiment, the rifaximin in the disclosed compositions, e.g., as in any one of the first through fourteenth embodiments, is present in an amount ranging from about 1% to about 15%, about 1% to about 5%, or about 2.5% to about 15%, or about 2.5% to about 12%, or about 5% to about 10%, or about 7% to about 15%, or about 7% to about 14%, or about 8% to about 14%, or about 8% to about 13%, or about 8% to about 12%, or about 8% to about 11%, or about 9% to about 12%, or about 9% to about 12%, or about 1% to about 12%, or 1% to about 10%, or about 1% to about 8%, or 2% to about 7%, 3% to about 7%, or 3% to about 6%, or 4% to about 5%, or present in an amount of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, or present in an amount of at most about 1%, at most about 2%, at most about 3%, at most about 4%, at most about 5%, at most about 6%, at most about 7%, at most about 8%, at most about 9%, at most about 10%, at most about 11%, at most about 12%, at most about 13%, at most about 14%, or at most about 15%, or present in an amount of about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, or about 15%, by weight of the composition.

In an alternative fifteenth embodiment, the rifaximin in the disclosed compositions, e.g., as in any one of the first through fourteenth embodiments, is present in an amount ranging from about 1% to about 15%, or about 2.5% to about 15%, or about 2.5% to about 12%, or about 5% to about 10%, or about 7% to about 15%, or about 7% to about 14%, or about 8% to about 14%, or about 8% to about 13%, or about 8% to about 12%, or about 8% to about 11%, or about 9% to about 12%, or about 9% to about 12%, or about 1% to about 12%, or 1% to about 10%, or about 1% to about 8%, or 2% to about 7%, 3% to about 7%, or 3% to about 6%, or 4% to about 5%, or present in an amount of at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15%, or present in an amount of at most about 1%, at most about 2%, at most about 3%, at most about 4%, at most about 5%, at most about 6%, at most about 7%, at most about 8%, at most about 9%, at most about 10%, at most about 11%, at most about 12%, at most about 13%, at most about 14%, or at most about 15%, or present in an amount of about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, or about 15%, by weight of the rifaximin, hydrogenated castor oil, and at least one additional solubilizing excipient.

In a sixteenth embodiment, the total amount of rifaximin in the disclosed composition, e.g., as in any one of the first through fifteenth embodiments, is less than about 125 mg (e.g., less than about 120 mg, less than about 110 mg, less than about 100 mg, less than about 90 mg, less than about 80 mg, less than about 70 mg, less than about 60 mg, less than about 50 mg, less than about 40 mg, less than about 30 mg, less than about 20 mg, or less than about 15 mg, less than about 10 mg, or less than about 9 mg, or less than about 8 mg, or less than about 7 mg, or less than about 6 mg, or less than about 5 mg, or less than about 4 mg, or less than about 3 mg, or less than about 2 mg, or less than about 1 mg, or less than about 0.5 mg). Alternatively, as part of a sixteenth embodiment, the total amount of rifaximin in the disclosed composition, e.g., as in any one of the first through fifteenth embodiments, ranges from about 1 mg to about 125 mg (e.g., about 1 mg to about 5 mg, about 2 mg to about 5 mg, about 3 mg to about 5 mg, about 3 mg to about 4 mg, about 1 mg to about 125 mg, about 5 mg to about 125 mg, about 10 mg to about 125 mg, about 10 mg to about 100 mg, about 25 mg to about 125 mg, about 25 mg to about 100 mg, about 25 mg to about 75 mg, about 30 mg to about 70 mg, about 35 mg to about 65 mg, about 40 mg to about 60 mg, about 45 mg to about 55 mg, about 75 mg to about 125 mg, about 80 mg to about 120 mg, 85 mg to about 115 mg, about 90 mg to about 110 mg, or about 95 mg to about 105 mg). Alternatively, as part of a sixteenth embodiment, the total amount (in milligrams) of rifaximin in the disclosed composition, e.g., as in any one of the first through fifteenth embodiments, is about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, or about 125 mg; or at least about 1, at least about 1.5, at least about 2, at least about 2.5, at least about 3, at least about 3.5, at least about 4, at least about 4.5, at least about 5, at least about 5.5, at least about 6, at least about 6.5, at least about 7, at least about 7.5, at least about 8, at least about 8.5, at least about 9, at least about 9.5, at least about 10, at least about 10.5, at least about 11, at least about 11.5, at least about 12, at least about 12.5, at least about 13, at least about 13.5, at least about 14, at least about 14.5, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50, at least about 51, at least about 52, at least about 53, at least about 54, at least about 55, at least about 56, at least about 57, at least about 58, at least about 59, at least about 60, at least about 61, at least about 62, at least about 63, at least about 64, at least about 65, at least about 66, at least about 67, at least about 68, at least about 69, at least about 70, at least about 71, at least about 72, at least about 73, at least about 74, at least about 75, at least about 76, at least about 77, at least about 78, at least about 79, at least about 80, at least about 81, at least about 82, at least about 83, at least about 84, at least about 85, at least about 86, at least about 87, at least about 88, at least about 89, at least about 90, at least about 91, at least about 92, at least about 93, at least about 94, at least about 95, at least about 96, at least about 97, at least about 98, at least about 99, at least about 100, at least about 101, at least about 102, at least about 103, at least about 104, at least about 105, at least about 106, at least about 107, at least about 108, at least about 109, at least about 110, at least about 111, at least about 112, at least about 113, at least about 114, at least about 115, at least about 116, at least about 117, at least about 118, at least about 119, at least about 120, at least about 121, at least about 122, at least about 123, at least about 124, or at least about 125 mg; or is at most about 1, at most about 1.5, at most about 2, at most about 2.5, at most about 3, at most about 3.5, at most about 4, at most about 4.5, at most about 5, at most about 5.5, at most about 6, at most about 6.5, at most about 7, at most about 7.5, at most about 8, at most about 8.5, at most about 9, at most about 9.5, at most about 10, at most about 10.5, at most about 11, at most about 11.5, at most about 12, at most about 12.5, at most about 13, at most about 13.5, at most about 14, at most about 14.5, at most about 15, at most about 16, at most about 17, at most about 18, at most about 19, at most about 20, at most about 21, at most about 22, at most about 23, at most about 24, at most about 25, at most about 26, at most about 27, at most about 28, at most about 29, at most about 30, at most about 31, at most about 32, at most about 33, at most about 34, at most about 35, at most about 36, at most about 37, at most about 38, at most about 39, at most about 40, at most about 41, at most about 42, at most about 43, at most about 44, at most about 45, at most about 46, at most about 47, at most about 48, at most about 49, at most about 50, at most about 51, at most about 52, at most about 53, at most about 54, at most about 55, at most about 56, at most about 57, at most about 58, at most about 59, at most about 60, at most about 61, at most about 62, at most about 63, at most about 64, at most about 65, at most about 66, at most about 67, at most about 68, at most about 69, at most about 70, at most about 71, at most about 72, at most about 73, at most about 74, at most about 75, at most about 76, at most about 77, at most about 78, at most about 79, at most about 80, at most about 81, at most about 82, at most about 83, at most about 84, at most about 85, at most about 86, at most about 87, at most about 88, at most about 89, at most about 90, at most about 91, at most about 92, at most about 93, at most about 94, at most about 95, at most about 96, at most about 97, at most about 98, at most about 99, at most about 100, at most about 101, at most about 102, at most about 103, at most about 104, at most about 105, at most about 106, at most about 107, at most about 108, at most about 109, at most about 110, at most about 111, at most about 112, at most about 113, at most about 114, at most about 115, at most about 116, at most about 117, at most about 118, at most about 119, at most about 120, at most about 121, at most about 122, at most about 123, at most about 124, or at most about 125 mg.

Alternatively, as part of an additional embodiment, the total amount (in milligrams) of rifaximin in the disclosed composition, e.g., as in any one of the first through sixteenth embodiments, is at least about 0.5, at least about 1.0, at least about 1.5, at least about 2.0, at least about 2.5, at least about 3.0, at least about 3.5, at least about 4.0, at least about 4.5, at least about 5.0, at least about 5.5, at least about 6.0, at least about 6.5, at least about 7.0, at least about 7.5, at least about 8.0, at least about 8.5, at least about 9.0, at least about 9.5, at least about 10.0, at least about 10.5, or at least about 11 mg, or at most about 0.5, at most about 1.0, at most about 1.5, at most about 2.0, at most about 2.5, at most about 3.0, at most about 3.5, at most about 4.0, at most about 4.5, at most about 5.0, at most about 5.5, at most about 6.0, at most about 6.5, at most about 7.0, at most about 7.5, at most about 8.0, at most about 8.5, at most about 9.0, at most about 9.5, at most about 10.0, at most about 10.5, or at most about 11 mg, or about 0.5, about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, about 10.0, about 10.5, or about 11 mg.

Liquid Composition

In a seventeenth embodiment, the compositions described herein, e.g., as in any one of the first through sixteenth embodiments, is a liquid composition.

3. Dosage Forms

For the purposes of administration, in certain embodiments, the compositions described herein may be administered as is or formulated as alternative dosage forms, e.g., for orally delivery. Formulations for oral delivery can be in the form of lozenges, aqueous or oily suspensions, emulsions, capsules, syrups, or elixirs. Orally administered compositions can comprise one or more optional agents, for example, sweetening agents such as fructose, aspartame or saccharin; flavoring agents such as peppermint, oil of wintergreen, or cherry; coloring agents; and preserving agents, to provide a pharmaceutically-palatable preparation. The compositions may be coated to delay disintegration and absorption in the gastrointestinal tract thereby providing a sustained action over an extended period of time.

In certain embodiments, the disclosed compositions are formulated in capsule dosage forms. In certain embodiments, the disclosed compositions are formulated in soft or hard capsule dosage forms. In certain embodiments, the disclosed compositions are formulated in soft or hard gelatin capsule dosage forms.

It should be noted that a specific dosage and treatment regimen for any particular patient will depend upon a variety of factors, including age, body weight, general health, sex, diet, time of administration, rate of excretion, drug combination, the judgment of the treating physician, and the severity of the particular disease being treated.

4. Methods of Use

The compositions described herein may be used in methods for treating or preventing diseases. For example, the invention described herein includes a method of treating or preventing a disease or disorder in a subject in need thereof. Such methods may include the step of administering to said subject a therapeutically effective amount of one or more of any of the aforementioned compositions, which may be in unit dosage form.

The compositions described herein are useful in treating one or more bowel related or liver function disorders. Such disorders include, for example, irritable bowel syndrome (IBS) (e.g., IBS-D), diarrhea, microbe associated diarrhea, infectious diarrhea, *Clostridium difficile* infections and symptoms (e.g., *Clostridium difficile* associated diarrhea), travelers' diarrhea, small intestinal bacterial overgrowth (SIBO), Crohn's disease, diverticular disease, pancreatitis (including chronic), pancreatic insufficiency, enteritis, colitis (e.g., ulcerative colitis, antibiotic associated colitis, and microscopic colitis), hepatic encephalopathy (or other diseases which lead to increased ammonia levels) and symptoms thereof, gastric dyspepsia, cirrhosis (e.g., alcoholic cirrhosis), polycystic liver disease, pouchitis, peritonitis, short bowel syndrome, inflammatory bowel disease, rosacea, sickle cell disease, and *H. pylori* infection.

In some embodiments, the compositions described herein are useful for the treatment and/or prevention of hepatic encephalopathy. For example, the compositions described herein may be useful for the treatment of hepatic encephalopathy reoccurrence; and/or for the treatment of overt hepatic encephalopathy; and/or for the prevention of overt hepatic encephalopathy.

The compositions described herein are useful for liver transplant preparation.

The compositions described herein are useful in treating cardiovascular conditions (e.g., atherosclerotic cardiovascular disease).

The compositions described herein are useful in treating disorders which affect the central nervous system and those associated with cognitive impairment such as Parkinson's disease, Alzheimer's disease, and autism.

The compositions described herein are useful in treating certain cancers such as acute myeloid leukemia.

The compositions described herein are useful in treating sickle cell disease and/or symptoms associated therewith.

Provided therefore, are methods of treating one or more bowel related or liver function disorders described herein in a subject in need thereof, comprising administering to the subject a therapeutically effective amount of a disclosed composition. Also provided is the use of a disclosed composition for the manufacture of a medicament for treating one or more bowel related or liver function disorders described herein. Further provided is the use of a disclosed composition for treating one or more bowel related or liver function disorders described herein.

In some embodiments, the methods described herein may include administering an aforementioned composition QD, BID, TID, or QID to a subject to provide a daily dose (in milligrams) of rifaximin to the subject in an amount of at least about 1.0, at least about 1.5, at least about 2.0, at least about 2.5, at least about 3.0, at least about 3.5, at least about 4.0, at least about 4.5, at least about 5.0, at least about 5.5, at least about 6.0, at least about 6.5, at least about 7.0, at least about 7.5, at least about 8.0, at least about 8.5, at least about 9.0, at least about 9.5, at least about 10.0, at least about 10.5, at least about 11.0, at least about 11.5, at least about 12.0, at least about 12.5, at least about 13.0, at least about 13.5, at least about 14.0, at least about 14.5, at least about 15.0, at least about 15.5, at least about 16.0, at least about 16.5, at least about 17.0, at least about 17.5, at least about 18.0, at least about 18.5, at least about 19.0, at least about 19.5, at least about 20.0, at least about 20.5, at least about 21.0, at least about 21.5, at least about 22.0, at least about 22.5, at least about 23.0, at least about 23.5, at least about 24.0, at least about 24.5, at least about 25.0, at least about 25.5, at least about 26.0, 26.5, at least about 27.0, at least about 27.5, at least about 28.0, at least about 28.5, at least about 29.0, at least about 29.5, at least about 30.0, at least about 30.5, at least about 31.0, at least about 31.5, at least about 32.0, at least about 32.5, at least about 33.0, at least about 33.5, at least about 34.0, at least about 34.5, at least about 35.0, at least about 35.5, at least about 36.0, at least about 36.5, at least about 37.0, at least about 37.5, at least about 38.0, at least about 38.5, at least about 39.0, at least about 39.5, or at least about 40.0 mg. In some embodiments, the methods described herein may include administering an aforementioned composition QD, BID, TID, or QID to a subject to provide a daily dose of rifaximin to the subject in an amount (in milligrams) of at most about 1.0, at most about 1.5, at most about 2.0, at most about 2.5, at most about 3.0, at most about 3.5, at most about 4.0, at most about 4.5, at most about 5.0, at most about 5.5, at most about 6.0, at most about 6.5, at most about 7.0, at most about 7.5, at most about 8.0, at most about 8.5, at most about 9.0, at most about 9.5, at most about 10.0, at most about 10.5, at most about 11.0, at most about 11.5, at most about 12.0, at most about 12.5, at most about 13.0, at most about 13.5, at most about 14.0, at most about 14.5, at most about 15.0, at most about 15.5, at most about 16.0, at most about 16.5, at most about 17.0, at most about 17.5, at most about 18.0, at most about 18.5, at most about 19.0, at most about 19.5, at most about 20.0, at most about 20.5, at most about 21.0, at most about 21.5, at most about 22.0, at most about 22.5, at most about 23.0, at most about 23.5, at most about 24.0, at most about 24.5, at most about 25.0, at most about 25.5, at most about 26.0, 26.5, at most about 27.0, at most about 27.5, at most about 28.0, at most about 28.5, at most about 29.0, at most about 29.5, at most about 30.0, at most about 30.5, at most about 31.0, at most about 31.5, at most about 32.0, at most about 32.5, at most about 33.0, at most about 33.5, at most about 34.0, at most about 34.5, at most about 35.0, at most about 35.5, at most about 36.0, at most about 36.5, at most about 37.0, at most about 37.5, at most about 38.0, at most about 38.5, at most about 39.0, at most about 39.5, or at most about 40.0 mg. In some embodiments, the methods described herein may include administering an aforementioned composition QD, BID, TID, or QID to a subject to provide a daily dose of rifaximin to the subject in an amount (in milligrams) of about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, about 10.0, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20.0, about 20.5, about 21.0, about 21.5, about 22.0, about 22.5, about 23.0, about 23.5, about 24.0, about 24.5, about 25.0, about 25.5, about 26.0, 26.5, about 27.0, about 27.5, about 28.0, about 28.5, about 29.0, about 29.5, about 30.0, about 30.5, about 31.0, about 31.5, about 32.0, about 32.5, about 33.0, about 33.5, about 34.0, about 34.5, about 35.0, about 35.5, about 36.0, about 36.5, about 37.0, about 37.5, about 38.0, about 38.5, about 39.0, about 39.5, or about 40.0 mg.

In some embodiments, the methods described herein may include administering an aforementioned composition at a dose of 3.5 mg, or 7.0 mg, or 10.5 mg BID to provide a daily dose of rifaximin to the subject in an amount of about 7.0 mg, or 14.0 mg, or 21.0 mg, respectively.

In some embodiments, the foregoing doses or daily doses may be provided by administering at least 1, 2, 3, 4, 5, 6, 7, 8, 9, or 10 unit dosage forms of the composition (e.g., capsules) to a subject per dose or per day, as the case may be. In some embodiments, the foregoing doses or daily doses may be provided by administering at most 1, 2, 3, 4, 5, 6, 7, 8, 9, or 10 unit dosage forms of the composition (e.g., capsules) to a subject per dose or per day, as the case may be. In some embodiments, the foregoing doses or daily doses may be provided by administering about 1, 2, 3, 4, 5, 6, 7, 8, 9, or 10 unit dosage forms of the composition (e.g., capsules) to a subject per dose or per day, as the case may be.

While certain embodiments of the invention have been described and/or exemplified above, various other embodiments will be apparent to those skilled in the art from this disclosure. The invention is, therefore, not limited to the particular embodiments described and/or exemplified, but is capable of considerable variation and modification without departure from the scope and spirit of the appended claims.

Exemplification

The representative examples that follow are intended to help illustrate the present disclosure, and are not intended to, nor should they be construed to, limit the scope of the invention.

1. Pre-Formulation Studies

A. Solubility

The solubility of rifaximin in various solubilizing excipients was investigated by adding excess amount of rifaximin in each solubilizing excipient to determine the saturation solubility. The amount of rifaximin dissolved was analyzed by HPLC. The results from the solubility screen are shown below in Table 1.

TABLE 1

| Solubilizing Excipient | Solubility (% w/w) | Solubilizing Excipient | Solubility (% w/w) |
|---|---|---|---|
| Diethylene glycol monoethyl ether grade HP | 21.25 | Glyceryl caprylate | 20.20 |
| Polyoxyl 40 hydrogenated castor oil | 20.30 | Castor oil | 17.10 |
| Polysorbate 80 | 19.90 | Glyceryl monooleate (Type 40) | 15.30 |
| Benzyl alcohol | 16.22 | Glyceryl monolinoleate | 15.00 |
| Polyethylene glycol 400 | 15.12 | Tri ethylene glycol | 14.62 |
| Diethyl sebacate | 11.22 | Oleyl alcohol | 10.27 |
| Polysorbate 20 | 9.27 | Oleic acid | 3.79 |
| Caprylic capric triglycerides | 2.00 | Propylene glycol | 0.73 |
| Sesame oil | 0.60 | Soybean oil | 0.55 |
| Corn oil | 0.30 | Diisopropyl adipate | 12.71 |
| Polyethylene glycol 600 | 21.20 | | |

B. Excipient Compatibility

To determine excipient compatibility, pre-determined amounts of rifaximin were added to each solvent and the resulting solutions were subjected to various temperature conditions for up to 4 weeks. Chemical purity was then analyzed via HPLC, the results of which are shown in Table 2.

TABLE 2

| | Rifaximin % Label Claim (LC) | | | | | | |
|---|---|---|---|---|---|---|---|
| | | T 2 weeks | | | T 4 weeks | | |
| Solvent | T0 | 25° C. | 40° C. | 50° C. | 25° C. | 40° C. | 50° C. |
| Castor Oil | 94.0 | 99.3 | 104.3 | 106.4 | 100.7 | 104.3 | 101.4 |
| Diethyl sebacate | 102.7 | 102.1 | 101.7 | 101.7 | 101.1 | 98.8 | 99.8 |
| Propylene glycol | 97.9 | 96.9 | 97.0 | 95.7 | 96.2 | 95.6 | 98.6 |
| Polyoxyl 40 hydrogenated castor oil | 102.7 | 100.0 | 100.0 | 97.4 | 101.3 | 99.4 | 96.1 |
| PEG 600 | 102.0 | 98.0 | 98.7 | 98.0 | 100.0 | 99.3 | 96.1 |
| Polysorbate 80 | 104.7 | 98.7 | 98.1 | 96.8 | 96.8 | 96.8 | 94.3 |
| Benzyl alcohol | 99.3 | 99.8 | 96.3 | 96.9 | 98.2 | 94.0 | 93.0 |
| Glyceryl monolinoleate | 102.7 | 98.7 | 100.0 | 97.4 | 100.6 | 100.0 | 92.9 |
| Triethylene glycol | 97.5 | 98.3 | 96.7 | 95.6 | 97.0 | 95.0 | 92.5 |
| Oleyl alcohol | 98.7 | 96.3 | 97.1 | 95.2 | 96.9 | 95.0 | 91.8 |
| Caprylic/capric triglyceride | 86.8 | 92.2 | 93.0 | 94.5 | NT | 92.0 | 89.3 |
| PEG 400 | 98.1 | 96.0 | 95.4 | 91.8 | 95.8 | 92.2 | 86.7 |
| diethylene glycol monoethyl ether grade P | 97.3 | 96.1 | 89.3 | 81.5 | 95.4 | 82.7 | 74.2 |
| Glyceryl monooleate | 92.7 | 96.4 | 58.3 | 48.9 | 95.0 | 59.0 | 41.7 |
| Diisopropyl adipate | 97.6 | 95.3 | 71.3 | 50.3 | 95.1 | 64.8 | 30.4 |

C. Compatibility with Gelatin Shells

The physical compatibility of individual excipients with gelatin shell matrix was investigated. For hard gelatin capsules, solvent was filled into hard capsules and placed in scintillation vials. For soft gelatin capsules, each capsule was dipped into the excipient and then placed in scintillation vials. The vials were then subjected to various temperature conditions for up to 4 weeks. Capsules were then evaluated for physical changes (softening or hardening of capsule shell).

Hard gel capsules were purchased from VWR (catalogue number 70102) with a volume of 0.68 mL, diameter of 6.63 mm, a length of 19.0 mm and size 1. Soft gel capsules were Advil liquid-gels, 200 mg strength, 80 counts. Results are shown in Tables 3 and 4.

TABLE 3

| Hard Gel Capsules | | | | | | |
|---|---|---|---|---|---|---|
| | Physical change (Yes or No) | | | | | |
| | T 2 weeks | | | T 4 weeks | | |
| Solvent | 25° C. | 40° C. | 50° C. | 25° C. | 40° C. | 50° C. |
| PEG 600 | No | No | No | No | No | No |
| PEG 400 | No | Yes | — | No | Yes | — |
| Polysorbate 80 | No | No | No | No | No | No |
| Castor oil | No | No | No | No | No | No |
| Polyoxyl 40 hydrogenated castor oil | No | No | No | No | No | No |
| Glyceryl monooleate | No | No | No | No | No | No |
| Glyceryl monolinoleate | No | No | No | No | No | No |
| Corn oil | No | No | No | No | No | No |
| diethylene glycol monoethyl ether grade HP | No | No | No | No | No | No |
| Diethyl sebacate | No | No | — | No | No | — |
| Benzyl alcohol | Yes | Yes | — | Yes | Yes | — |
| Triethylene glycol | Yes | Yes | — | Yes | Yes | — |
| Oleyl alcohol | No | No | — | No | No | — |
| Caprylic/capric triglyceride | No | No | — | No | No | — |

TABLE 4

| Soft Gel Capsules | | | | | | |
|---|---|---|---|---|---|---|
| | Physical Change (Yes or No) | | | | | |
| | T 2 weeks | | | T 4 weeks | | |
| Solvent | 25° C. | 40° C. | 50° C. | 25° C. | 40° C. | 50° C. |
| PEG 600 | No | No | No | No | No | No |
| Polysorbate 80 | No | No | No | No | No | No |
| Castor oil | No | No | No | No | No | No |
| Polyoxyl 40 Hydrogenated castor oil | No | No | Yes | No | No | Yes |

TABLE 4-continued

| Soft Gel Capsules | | | | | | |
|---|---|---|---|---|---|---|
| | Physical Change (Yes or No) | | | | | |
| | T 2 weeks | | | T 4 weeks | | |
| Solvent | 25° C. | 40° C. | 50° C. | 25° C. | 40° C. | 50° C. |
| PEG 400 | No | No | No | No | No | No |
| Glyceryl monooleate | No | Yes | Yes | No | Yes | Yes |
| Glyceryl monolinoleate | No | No | No | No | No | No |

2. Formulation Studies

A. Evaluation of Percent of Soluble Drug Available

The percent of drug (rifaximin) soluble in phosphate buffer (pH ~6.8) or simulated intestinal fluid (SIF, pH ~6.8) was investigated using the following criteria. The control species was Xifaxan® tablet (200 mg) or Xifaxan® powder (200 mg API+glyceryl distearate—to represent enteric coated tablet.) Additives, where noted, included bile acid (cholic acid), butylated hydroxytoluene (BHT), and isooctyl acrylate/acrylamide/vinyl acetate copolymer (Kollidon® VA64).

Compositions were made by weighing the hydrogenated castor oil and at least one additional solubilizing excipient followed by mixing. Where applicable, BHT was then added to the mixture and dissolved. Rifaximin was added last.

Figure 2:
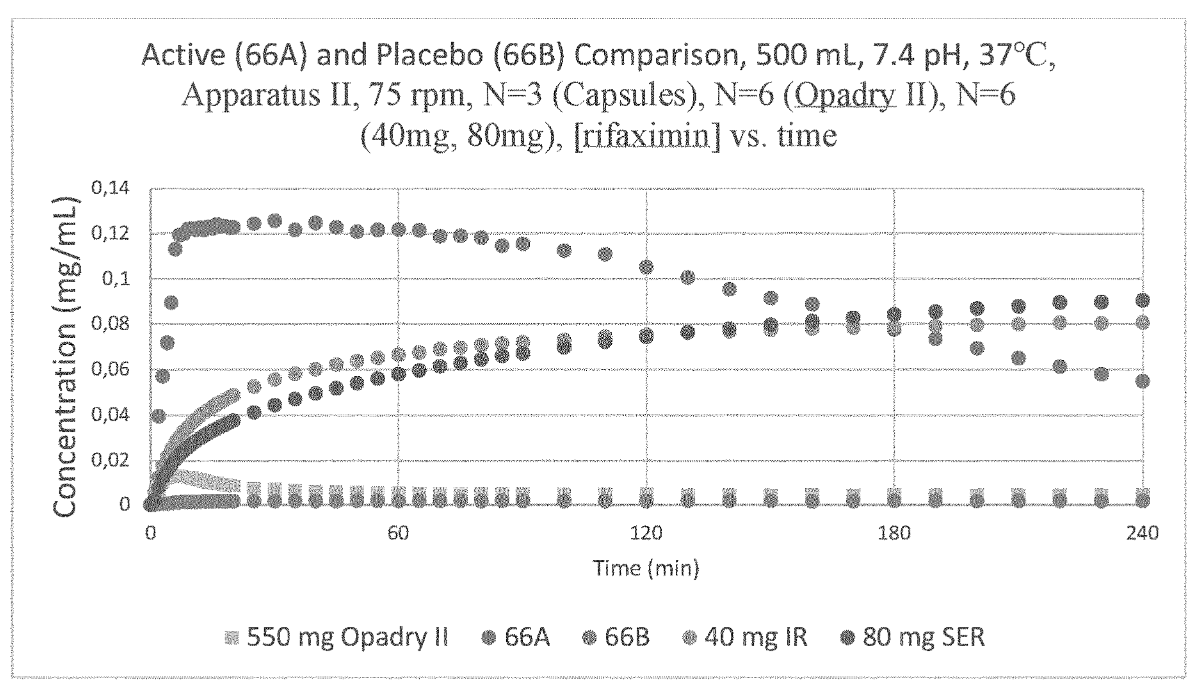
FIG. 2. shows the dissolution results for inventive composition 5425-66A compared with placebo (i.e., no rifaximin) 5425-66B, Xifaxan 550 mg (Opadry II), and 40 mg and 80 mg solid dispersion formulations as described in WO 2018/064472.
Figure 3:
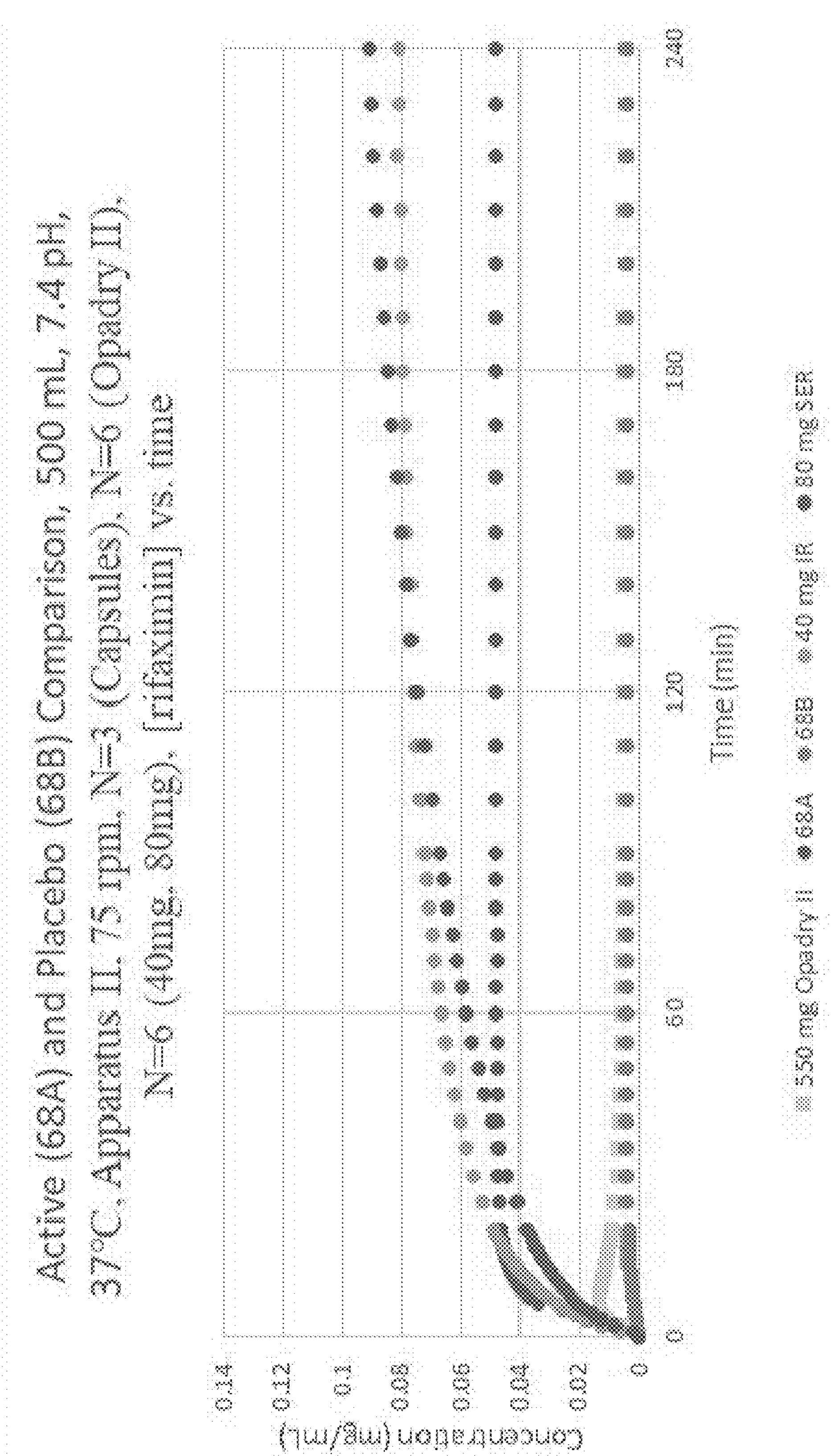
FIG. 3. shows the dissolution results for inventive composition 5425-68A at pH 7.4 compared with placebo (i.e., no rifaximin) 5425-68B, Xifaxan 550 mg (Opadry II), and 40 mg and 80 mg solid dispersion formulations as described in WO 2018/064472.
Figure 4:
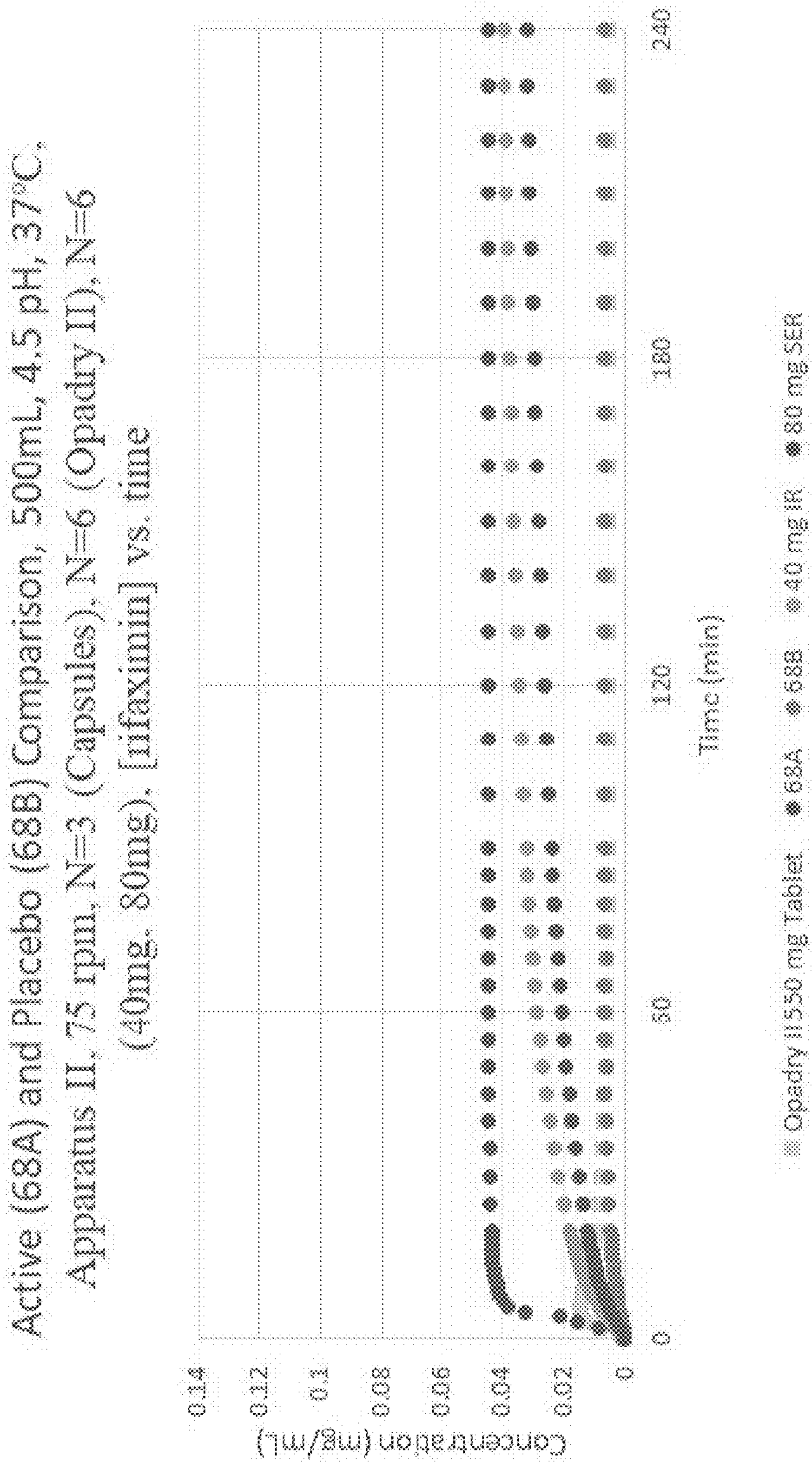
FIG. 4. shows the dissolution results for inventive composition 5425-68A at pH 4.5 compared with placebo (i.e., no rifaximin) 5425-68B, Xifaxan 550 mg (Opadry II), and 40 mg and 80 mg solid dispersion formulations as described in WO 2018/064472.
Figure 5:
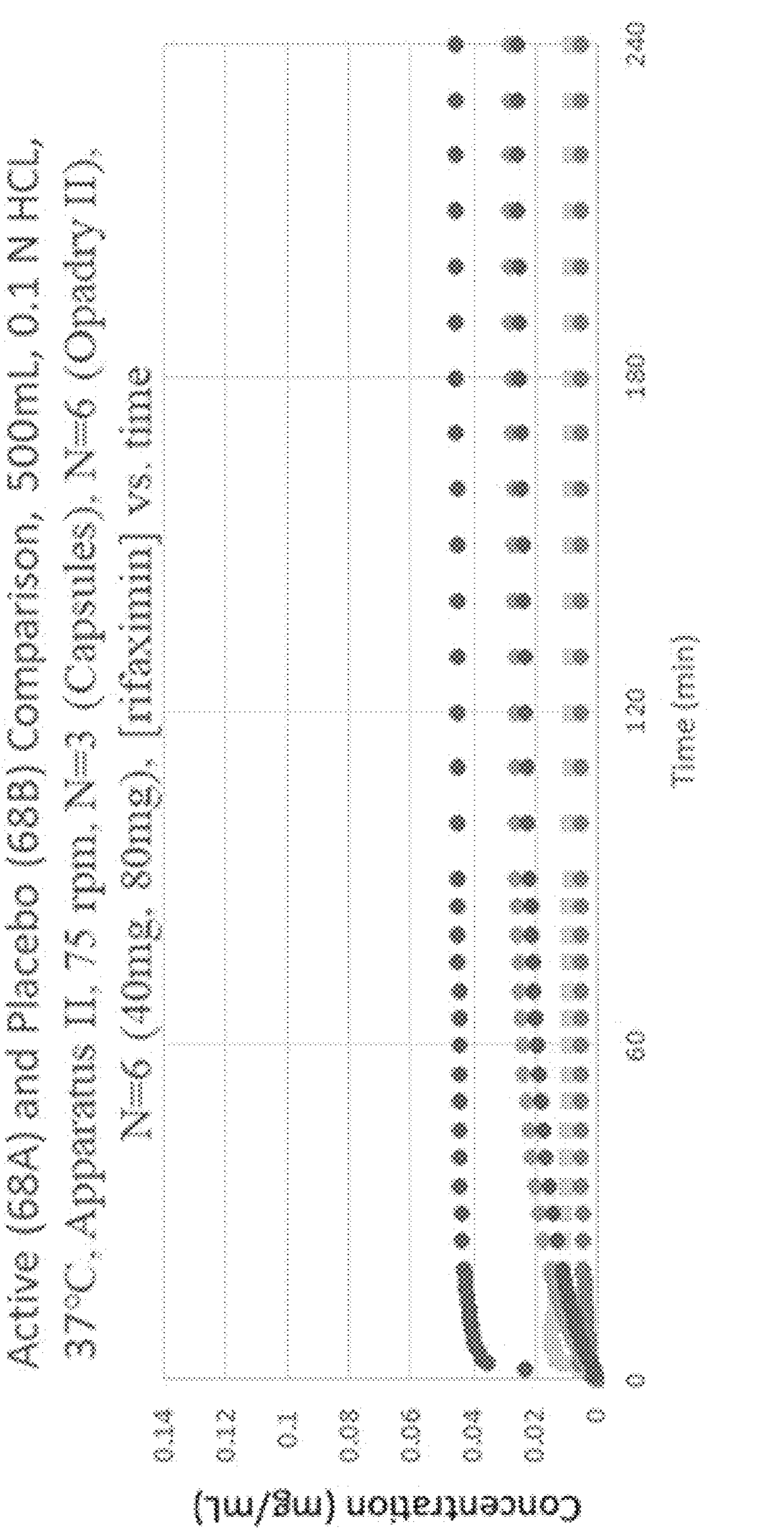
FIG. 5. shows the dissolution results for inventive composition 5425-68A at 0.1N HCl compared with placebo (i.e., no rifaximin) 5425-68B, Xifaxan 550 mg (Opadry II), and 40 mg and 80 mg solid dispersion formulations as described in WO 2018/064472.
Figure 6:
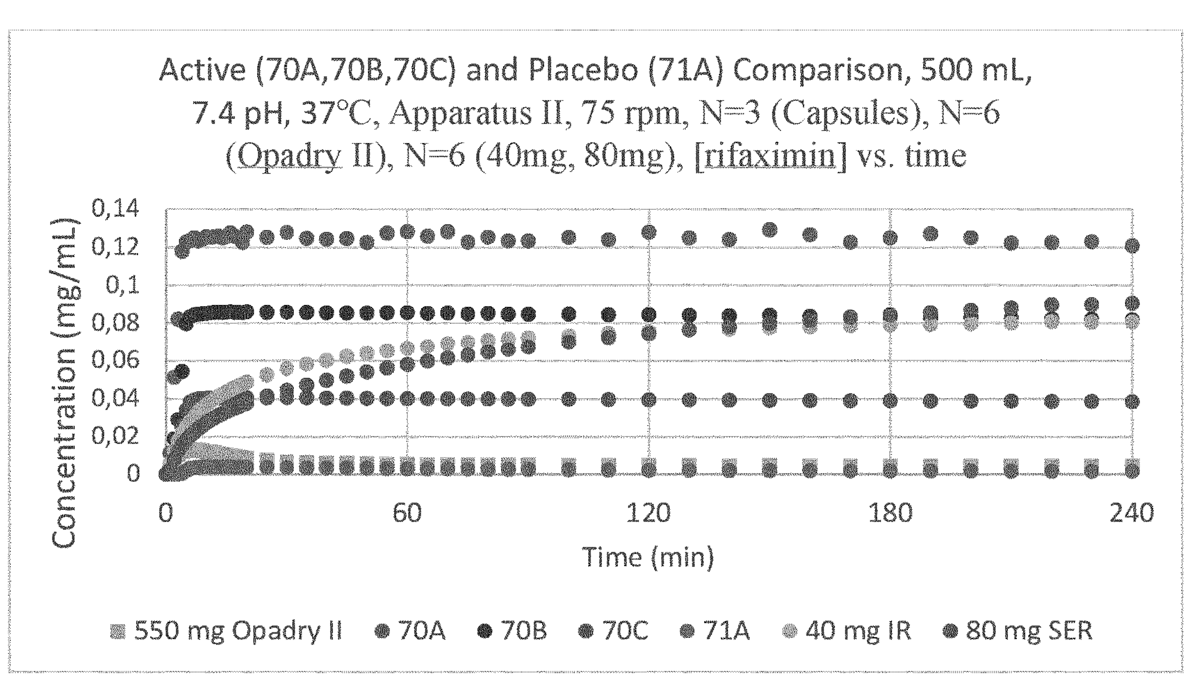
FIG. 6. shows the dissolution results for inventive composition 5425-70A, 5425-70B, and 5425-70C at pH 7.4 compared with placebo (i.e., no rifaximin) 5425-66B, Xifaxan 550 mg (Opadry II), and 40 mg and 80 mg solid dispersion formulations as described in WO 2018/064472.
Figure 7:
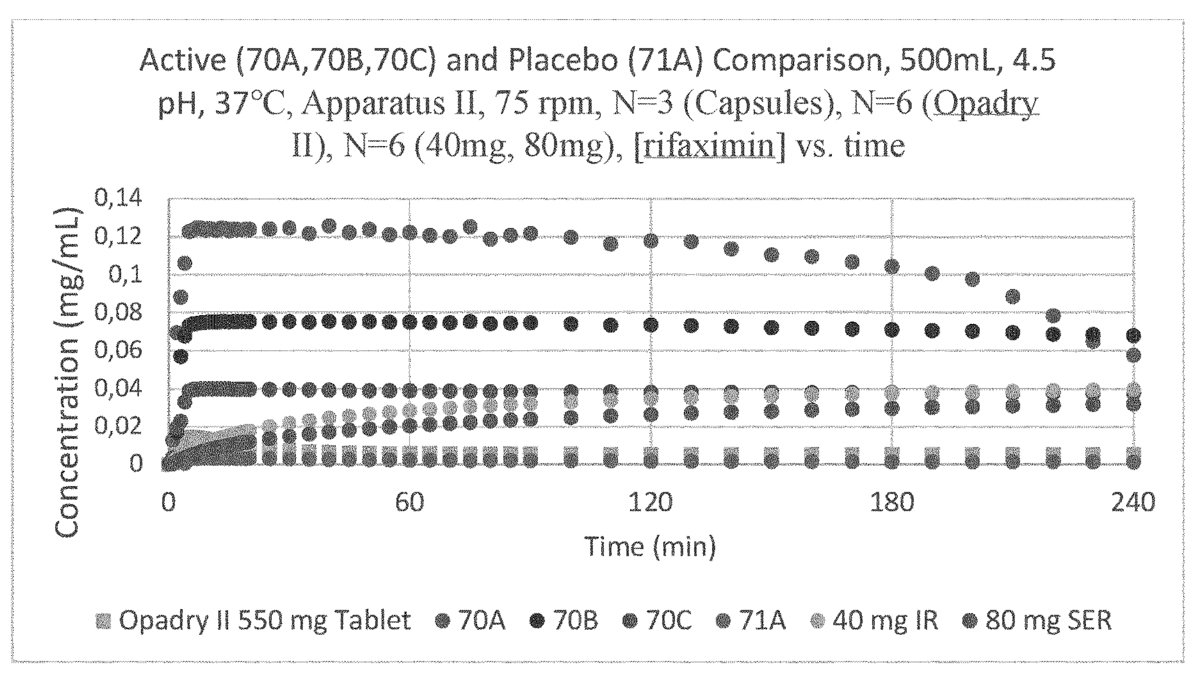
FIG. 7. shows the dissolution results for inventive composition 5425-70A, 5425-70B, and 5425-70C at pH 4.5 compared with placebo (i.e., no rifaximin) 5425-66B, Xifaxan 550 mg (Opadry II), and 40 mg and 80 mg solid dispersion formulations as described in WO 2018/064472.
Figure 8:
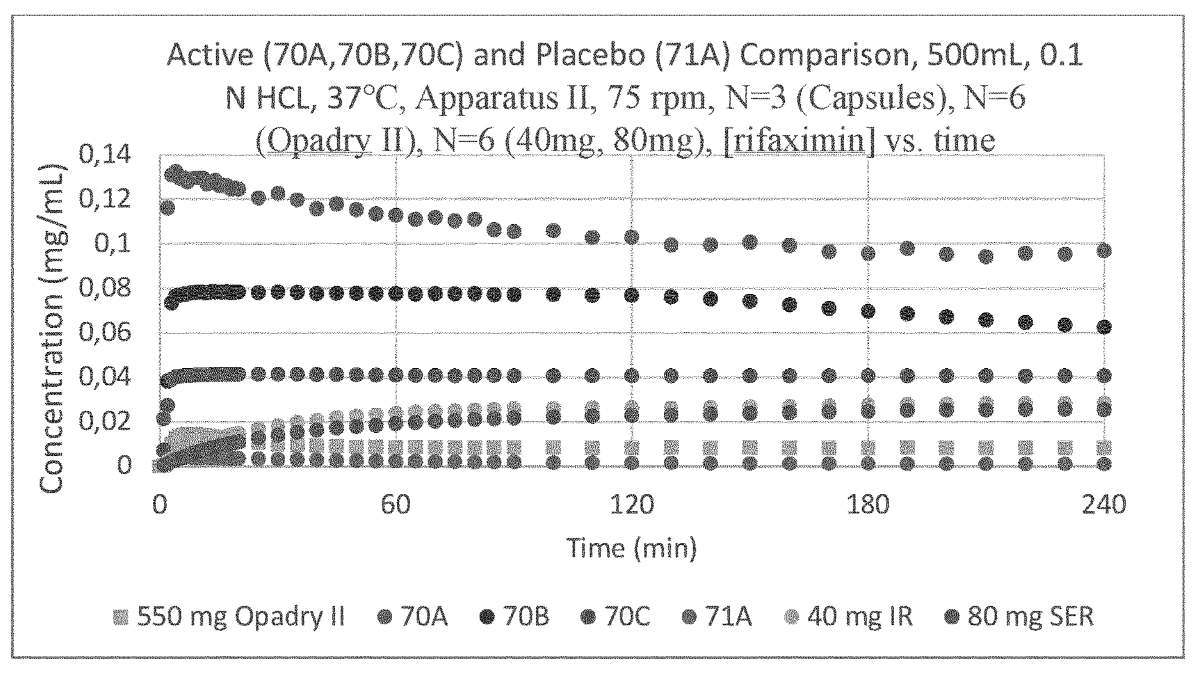
FIG. 8. shows the dissolution results for inventive composition 5425-70A, 5425-70B, and 5425-70C at 0.1N HCl compared with placebo (i.e., no rifaximin) 5425-66B, Xifaxan 550 mg (Opadry II), and 40 mg and 80 mg solid dispersion formulations as described in WO 2018/064472.

Dissolution studies were performed to evaluate the percent drug solubilized over a period of time from Rifaximin SEDDS formulations as compared to Xifaxan at pH 7.4 buffer, 37 degrees Celsius. Samples were analyzed via HPLC. Results are shown below in Table 5 as well as FIG. 1 and FIG. 2. As shown in the figures, dissolution of the inventive formulations (5425-66A; 70 mg rifaximin and 5425-67A; 35 mg rifaximin) was significantly faster than previously disclosed 40 mg rifaximin IR and 80 mg rifaximin SER solid dispersion compositions (see WO 2018/064472) and Xifaxan 550 mg.

TABLE 5

| | % w/w | |
|---|---|---|
| Batch No. | 5425-66A | 5425-67A |
| API concentration | 10% API | 5% API |
| Rifaximin | 10.00 | 5.00 |
| Castor Oil | 10.00 | 15.00 |
| Polyoxyl 40 Hydrogenated Castor Oil | 34.96 | 34.96 |
| Glyceryl Caprylate Type 1 | 12.00 | 12.00 |
| Polysorbate (Tween) 80 | 33.00 | 33.00 |
| Butylated Hydroxytoluene (BHT) | 0.04 | 0.04 |
| Total | 100.00 | 100.00 |
| Ratio of % Drug soluble as compared to Xifaxan at 1 hour, pH 7.4 buffer | 71.59 | 35.42 |

For SIF, prototype compositions (1 gram total, each comprising 100 mg of API) or Xifaxan® powder were mixed at 37° C. for 1 hour in SIF (100 mL). The mixture was then centrifuged for 20 min and analyzed via HPLC. Results are shown below in Table 6A and 6B.

TABLE 6A

| Percent Soluble Drug in Phosphate Buffer | | | | | | | |
|---|---|---|---|---|---|---|---|
| Ingredient | 5256-27C | 5394-58A | 5256-34E | 5394-57A w/w % | 5256-35A | 5394-60A | Xifaxan ® powder |
| Rifaximin | 10.0 | 5.00 | 10.0 | 5.00 | 10.0 | 5.00 | 200 mg |
| Castor oil | 10.0 | 15.00 | — | — | — | — | — |
| Glyceryl caprylate | 12.0 | 12.00 | — | — | — | — | — |
| Polysorbate (Tween) 80 | 33.0 | 33.0 | — | — | — | — | — |
| Polyoxyl 40 Hydrogenated Castor | 34.96 | 34.96 | 35.0 | 19.96 | 34.96 | 39.96 | — |
| Diethyl Sebacate | — | — | 27.5 | 37.50 | 27.5 | 27.50 | — |
| Diethylene glycol monoethyl ether | — | — | 27.5 | 37.50 | 27.5 | 27.50 | — |
| Butylated hydroxytoluene | 0.038 | 0.038 | — | 0.038 | 0.038 | 0.038 | — |
| Glyceryl distearate | — | — | — | — | — | — | 18 mg |
| Total | 100.00 | 100.00 | 100.00 | 100.00 | 100.00 | 100.00 | 218.00 |
| Percent of drug soluble (% w/w) | 0.0131 | 0.0503 | 0.0021 | 0.0064 | 0.0024 | 0.0065 | 0.0003 |
| Ratio of inventive comp. as compared to Xifaxan ® | 44.00 | 168.00 | 7.00 | 21.00 | 8.00 | 22.00 | 1.00 |

TABLE 6B

| Percent Soluble Drug in SIF | | | | |
|---|---|---|---|---|
| | Phosphate Buffer | | SIF | |
| Ingredients | 5256-34E | Xifaxan ® powder | 5256-34E % w/w | Xifaxan ® |
| Rifaximin | 10.0 | 200 mg | 10.0 | Colloidal silicon dioxide, disodium edetate, glycerol palmitostearate, hypromellose |
| Polyoxyl 40 Hydrogenated castor oil | 35.0 | — | 35.0 | |
| Diethyl sebacate | 27.5 | — | 27.5 | |
| Diethylene glycol monoethyl ether | 27.5 | — | 27.5 | |
| Butylated hydroxytoluene | — | — | — | |
| Total | 100.0 | 218.00 | 100.0 | |

TABLE 6B-continued

| Percent Soluble Drug in SIF | | | | |
|---|---|---|---|---|
| | Phosphate Buffer | | SIF | |
| Ingredients | 5256-34E | Xifaxan ® powder | 5256-34E % w/w | Xifaxan ® |
| Percent of drug soluble (% w/w) | 0.0021 | 0.0003 | 0.0057 | 0.001 |
| Ratio of inventive comp, as compared to Xifaxan ® | 7.00 | 1.00 | 6.00 | 1.00 |

The effects from the inclusion of certain additives such as butylated hydroxytoluene (BHT), crystallization inhibitor (CI), and bile acid are shown in Table 7. Similar to the above, the inventive compositions in Table 7 comprised 1 gram total, each comprising 100 mg of rifaximin.

TABLE 7

| Effect of Additives | | | | | | | |
|---|---|---|---|---|---|---|---|
| Ingredients | No BHT 5256-34E | BHT 5256-34E | No CI 5256-35A | CI 5256-35A % w/w | No Bile acid 5246-34E | Bile acid 5256-34E | Xifaxan powder |
| Rifaximin | 10.0 | 10.0 | 10.0 | 10.0 | 10.0 | 10.0 | 200 mg |
| Polyoxyl 40 hydrogenated castor oil | 35.0 | 34.96 | 34.96 | 29.962 | 35.0 | 34.8 | — |
| Diethyl Sebacate | 27.5 | 27.5 | 27.5 | 27.5 | 27.5 | 27.5 | — |
| Diethylene glycol monoethyl ether | 27.5 | 27.5 | 27.5 | 27.5 | 27.5 | 27.5 | — |

TABLE 7-continued

| Effect of Additives | | | | | | | |
|---|---|---|---|---|---|---|---|
| Ingredients | No BHT 5256-34E | BHT 5256-34E | No CI 5256-35A | CI 5256-35A % w/w | No Bile acid 5246-34E | Bile acid 5256-34E | Xifaxan powder |
| Butylated hydroxytoluene | — | 0.038 | 0.038 | 0.038 | — | — | — |
| Isooctyl acrylate/acrylamide/vinyl acetate copolymer (Koilidone ® VA 64) | — | — | — | 5.0 | — | — | — |
| Glyceryl distearate | — | — | — | — | — | — | 18 mg |
| Cholic acid | — | — | — | — | — | 0.2 | — |
| Total | 100.0 | 100.0 | 100.0 | 100.0 | 100.0 | 100.0 | 218.00 |
| Percent of drug soluble (% w/w) | 0.0021 | 0.0024 | 0.0024 | 0.0016 | 0.0021 | 0.0014 | 0.0003 |
| Ratio of inventive comp. as compared to Xifaxan | 7.00 | 8.00 | 8.00 | 5.00 | 7.00 | 5.00 | 1.00 |

B. Prototype Compatibility with Gelatin Shells

The compatibility of certain inventive compositions with gelatin shell matrix was investigated. Capsules were size 1, VWR catalogue number 70102. The vials were then subjected to various temperature conditions for up to 5 weeks. Capsules were then evaluated for physical changes (softening or hardening of capsule shell). Results from this study are shown in Table 8 below. The inventive compositions in Table 7 comprised 1 gram total, each comprising 50 mg or 100 mg of rifaximin.

TABLE 8

| Ingredients | 5256-27C | 5394-58A | 5256-34E % w/w | 5394-57A | 5256-35A | 5394-60A |
|---|---|---|---|---|---|---|
| Rifaximin | 10.0 | 5.00 | 10.0 | 5.00 | 10.0 | 5.00 |
| Castor oil | 10.0 | 15.00 | — | — | — | — |
| Glyceryl caprylate | 12.0 | 12.00 | — | — | — | — |
| Polysorbate 80 | 33.0 | 33.00 | — | — | — | — |
| Polyoxyl 40 hydrogenated castor | 34.96 | 34.96 | 35.0 | 19.96 | 34.96 | 39.96 |
| Diethyl sebacate | — | — | 27.5 | 37.50 | 27.5 | 27.50 |
| Diethylene glycol monoethyl ether | — | — | 27.5 | 37.50 | 27.5 | 27.50 |
| butylated hydroxytoluene | 0.038 | 0.038 | — | 0.038 | 0.038 | 0.038 |
| Total | 100.00 | 100.00 | 100.00 | 100.00 | 100.00 | 100.00 |
| Percent of drug soluble (% w/w) | 0.0131 | 0.0503 | 0.0021 | 0.0064 | 0.0024 | 0.0065 |
| Ratio of inventive comp. as compared to Xifaxan ® | 44.00 | 168.00 | 7.00 | 21.00 | 8.00 | 22.00 |
| Hard gel compatibility | Yes | Yes | Yes | Yes | Yes | Yes |
| Soft gel compatibility | TBD | Yes | No | No | No | No |

As shown above, inventive compositions significantly improve the solubility of rifaximin under conditions similar to those present in vivo. In some cases, this effect represents over a 150-fold increase in percent soluble rifaximin when compared to commercially available Xifaxan®.

3. Additional Formulations

Additional formulations are shown below in Table 9.

TABLE 9

| Ingredients | 5507-65A | 5425-68A | 5425-70A | 5425-70B | 5425-70C | A |
|---|---|---|---|---|---|---|
| | % wt/wt | | | | | |
| Rifaximin | 10.0 | 2.5 | 10.0 | 5.0 | 2.5 | 2.5 |
| Castor oil | 10.0 | 17.5 | — | — | — | 10.0 |
| Polyoxyl 40 hydrogenated castor oil (RH-40) | 34.90 | 34.962 | 34.96 | 39.96 | 42.46 | 35.0 |
| Glyceryl caprylate type I | 12.0 | 12.0 | — | — | — | 12.0 |
| Polysorbate (Tween) 80 | 33.0 | 33.0 | — | — | — | 40.29 |
| Butylated Hydroxytoluene (BHT) | 0.05 | 0.038 | 0.038 | 0.038 | 0.038 | 0.1 |
| Citric acid | 0.05 | — | — | — | — | 0.01 |
| Ascorbyl Palmitate | — | — | — | — | — | 0.1 |
| Diethyl Sebacate | — | — | 16.5 | 16.5 | 16.5 | — |
| Diethylene glycol monoethyl ether | — | — | 38.5 | 38.5 | 38.5 | — |
| Total | 100.0 | 100.0 | 100.0 | 100.0 | 100.0 | 100.0 |

Compositions may be placed in non-enteric coated capsules such as Quali-G, Size 4, 140 mg fill. Dissolution results for 5425-68A, 5425-70A, 5425-70B, and 5425-70C under various pH conditions are shown in FIGS. 3-8, as compared to previously disclosed 40 mg rifaximin IR and 80 mg rifaximin SER solid dispersion compositions (see WO 2018/064472) and Xifaxan 550 mg.

4. Anti-Bacterial Activity

The antibacterial properties of representative compositions were examined as set forth herein.

Organisms were prepared by inoculating the surface of Soybean-Casein Digest Agar (TSA) plates, incubated at 30 to 35° C. for 18 to 24 hours. Following the incubation period, the plates were washed with sterile Serological Saline Solution to harvest the microorganisms used and dilutions with Saline were made, plated on TSA and incubated at 30 to 35° C. for 18-24 hours to determine the concentration. The inoculum level was then adjusted to 10^ cfW mL for use as a stock suspension. Stock suspensions were well mixed and homogenized at each inoculation interval.

The following microorganisms were used in this Kill Time Study *Escherichia coli* ATCC 8739, *Shigella flexneri* ATCC 12022, and *Salmonella choleraesuis* ATCC 10708. Positive controls were performed at initiation and completion by pour plating to enumerate inoculum levels and verify culture purity during testing and Negative controls were performed to establish sterility of media, reagents, and materials used at initiation. Neutralizer Suitability using Modified Letheen Broth (MLB) was performed concurrently with Kill Time testing to confirm the recovery of <100 CFU of the test organism in the subculture media in the presence of product.

1.0 gram of formula (5507-65A) was weighted. In a separate container, a mixture of 70 ml 0.1 N Hydrochloric acid (pH 1.1) and 30 ml of 0.20 M tribasic sodium phosphate was made and the pH was adjusted to about 6.8. The mixture was added to the formula and agitated for 1 hour at room temperature. Then the mixture was filtered through 0.45 micron filter to remove any precipitate and to collect the filtrate. Duplicate 10 mL containers for each treated specimen or material concentration was prepared, equilibrated to 25±2° C., and 0.1 mL of inoculum was added to each container to achieve a final concentration of 10^ CFU/mL into the product.

Figure 9:
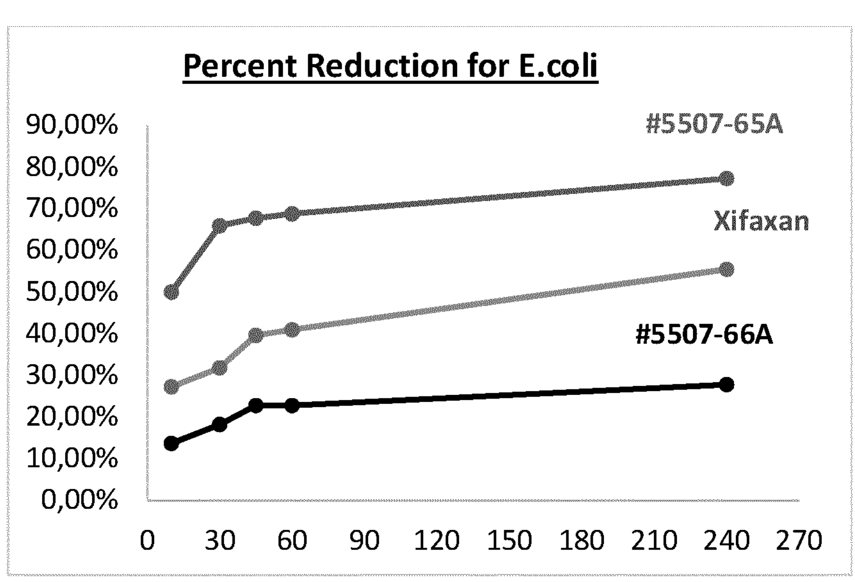
FIG. 9 shows the percent reduction, as a function of time (minutes), for *E. coli* after treatment with inventive formulation 5507-65A compared to placebo and Xifaxan 550 mg.
Figure 10:
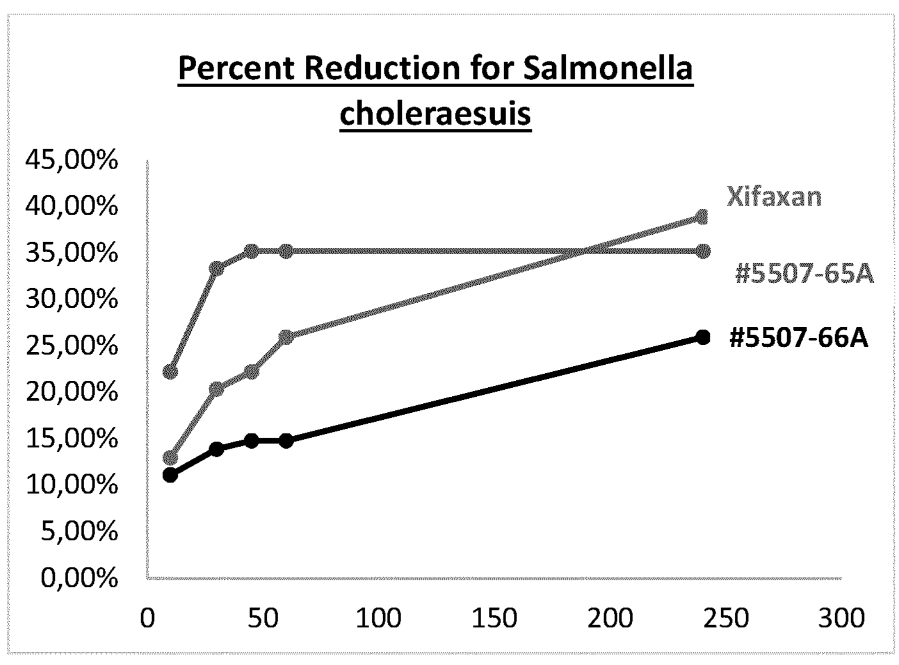
FIG. 10 shows the percent reduction, as a function of time (minutes), for *Salmonella choleraesuis* after treatment with inventive formulation 5507-65A compared to placebo and Xifaxan 550 mg.
Figure 11:
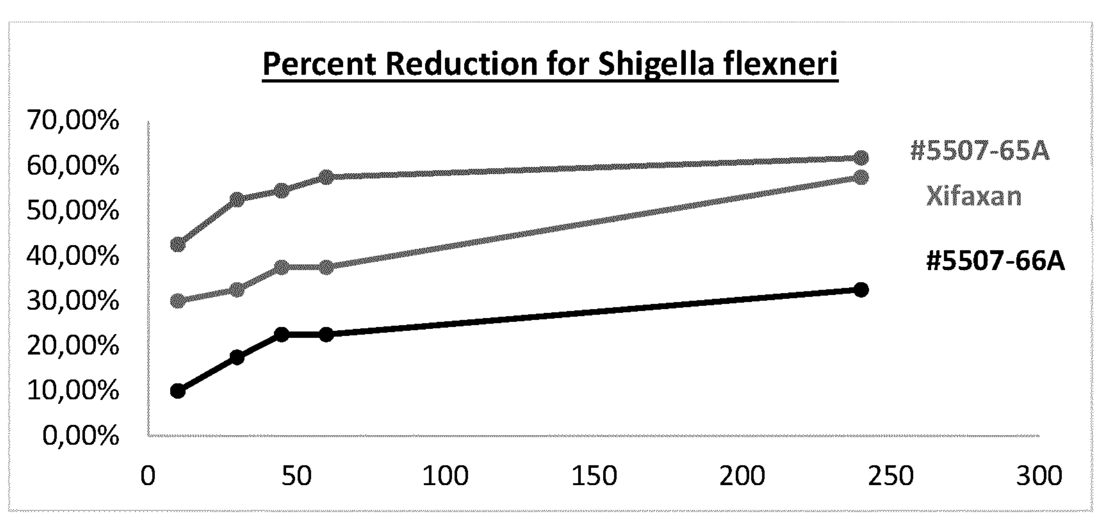
FIG. 11 shows the percent reduction, as a function of time (minutes), for *Shigella flexneri* after treatment with inventive formulation 5507-65A compared to placebo and Xifaxan 550 mg.

Serial dilutions from each replicate were made at intervals of 10 minutes, 30 minutes, 45 minutes, 1 hour, 2 hours, 3 hours, and 4 hours using 1 ml of the inoculated test product into 9 ml MLB from 1:10 to 1:1000000. Subsequently, 1 mL from each dilution was pour plated with TSA in duplicate, incubated at 30 to 35° C. for 48 hours. After the incubation period, all plates were counted to determine the number of microorganisms, results are averaged and reported as log reductions. A placebo control (5507-66A) of formulation 5507-65A was prepared in the same manner. The placebo contained no rifaximin and comprised 44.90% wt/wt of polyoxyl 40 hydrogenated castor oil instead of 34.90% wt/wt. A Xifaxan 550 mg tablet was also tested and compared. Results are shown in FIGS. 9-11.

5. Stability Studies

A stability study was performed to determine whether rifaximin would degrade in a representative liquid composition described herein during storage. The formulation of Table 10 was stored at 5° C. and at 25° C. (at 60% RH) and inspected at 0.5 and 1.0 month for changes in visual appearance and concentration of rifaximin by LC-MS. The results of such study are shown in Table 11, which indicate that little or no degradation of rifaximin was observed in the representative liquid composition.

TABLE 10

| Ingredients | % w/w |
|---|---|
| Rifaximin | 2.50 |
| Castor oil | 10.00 |
| Polyoxyl 40 Hydrogenated Castor Oil | 35.00 |
| Glyceryl Caprylate Type I | 12.00 |
| Polysorbate (Tween) 80 | 40.29 |

TABLE 10-continued

| Ingredients | % w/w |
|---|---|
| Butylated Hydroxytoluene | 0.10 |
| Anhydrous Citric Acid | 0.01 |
| Ascorbyl Palmitate | 0.10 |
| Total | 100.00 |

TABLE 11

| Storage Conditions | Time Point | Description (Visual) | Rifaximin % LC |
|---|---|---|---|
| N/A | Initial | Conforms | 100.20 |
| 5° C. | 0.5 Month | Conforms | 101.00 |
| | 1 M | Conforms | 100.10 |
| 25° C./60% RH | 0.5 Month | Conforms | 99.10 |
| | 1 M | Conforms | 100.00 |

The contents of all references (including literature references, issued patents, published patent applications, and co-pending patent applications) cited throughout this application are hereby expressly incorporated herein in their entireties by reference.

The invention claimed is:

1. A pharmaceutically acceptable composition comprising rifaximin, a hydrogenated castor oil in an amount ranging from about 25% to about 65% by weight of the composition, and at least one additional solubilizing excipient comprising a combination of castor oil, glyceryl caprylate, and polysorbate 80.

2. The composition of claim 1, wherein the hydrogenated castor oil is polyoxyl 60 hydrogenated castor oil or polyoxyl 40 hydrogenated castor oil.

3. The composition of claim 1, wherein the at least one additional solubilizing excipient further comprises polyethylene glycol 600, benzyl alcohol, polyethylene glycol 400, diethylene glycol monoethyl ether, glyceryl monooleate, triethylene glycol, diisopropyl adipate, diethyl sebacate, olelyl alcohol, polysorbate 20, oleic acid, caprylic capric triglycerides, propylene glycol, sesame oil, soybean oil, and corn oil, and combinations thereof.

4. The composition of claim 1, wherein the at least one additional solubilizing excipient is present in an amount ranging from about 45% to about 65% by weight of the composition.

5. The composition of claim 1, wherein the castor oil is present in an amount ranging from about 5% to about 15% by weight of the composition;

the glyceryl caprylate is present in an amount ranging from about 5% to about 15% by weight of the composition; and the polysorbate 80 is present in an amount ranging from about 20% to about 40% by weight of the composition.

6. The composition of claim 1, wherein the castor oil is present in an amount ranging from about 10% to about 20% by weight of the composition;

the glyceryl caprylate is present in an amount ranging from about 5% to about 15% by weight of the composition; and the polysorbate 80 is present in an amount ranging from about 20% to about 40% by weight of the composition.

7. The composition of claim 1, wherein the castor oil is present in an amount ranging from about 5% to about 15% by weight of the composition;

the glyceryl caprylate is present in an amount ranging from about 10% to about 15% by weight of the composition; and the polysorbate 80 is present in an amount ranging from about 35% to about 45% by weight of the composition.

8. The composition of claim 1, wherein the at least one additional solubilizing excipient further comprises a combination of diethyl sebacate and diethylene glycol monoethyl ether.

9. The composition of claim 8, wherein the diethyl sebacate is present in an amount ranging from about 20% to about 35% by weight of the composition; and the diethylene glycol monoethyl ether is present in an amount ranging from about 20% to about 35% by weight of the composition.

10. The composition of claim 8, wherein the diethyl sebacate is present in an amount ranging from about 10% to about 20% by weight of the composition; and the diethylene glycol monoethyl ether is present in an amount ranging from about 30% to about 45% by weight of the composition.

11. The composition of claim 1, wherein the composition further comprises an antioxidant and/or a chelating agent.

12. The composition of claim 1, wherein the composition further comprises one or more of butylated hydroxytoluene (BHT) and citric acid, each in an amount ranging from about 0.01% to about 0.1% by weight of the composition.

13. The composition of claim 1, wherein the composition further comprises one or more of butylated hydroxytoluene (BHT), citric acid, and ascorbyl palmitate, each in an amount ranging from about 0.05% to about 0.15% by weight of the composition.

14. The composition of claim 1, wherein the rifaximin is present in an amount ranging from about 1.0% to about 15% by weight of the composition.

15. The composition of claim 1, wherein the rifaximin is present in an amount ranging from about 1% to about 5% by weight of the composition.

16. The composition of claim 1, wherein the rifaximin is present in an amount of about 2.5% by weight of the composition.

17. The composition of claim 1, wherein the total amount of rifaximin in the composition ranges from about 1 mg to about 50 mg.

18. The composition of claim 1, wherein the composition comprises about 10% rifaximin, about 10% castor oil, about 12% glyceryl caprylate, about 33% polysorbate 80, and about 35% polyoxyl 40 hydrogenated castor oil, by weight of the composition.

19. The composition of claim 1, wherein the composition comprises about 5% rifaximin, about 15% castor oil, about 12% glyceryl caprylate, about 33% polysorbate 80, and about 35% polyoxyl 40 hydrogenated castor oil, by weight of the composition.

20. The composition of claim 1, wherein the composition comprises about 2.5% rifaximin, about 10% castor oil, about 12% glyceryl caprylate, about 40% polysorbate 80, and about 35% polyoxyl 40 hydrogenated castor oil, by weight of the composition.

21. The composition of claim 1, wherein the composition is a liquid composition.

* * * * *